United States Patent
Avisar

(10) Patent No.: US 8,831,924 B2
(45) Date of Patent: Sep. 9, 2014

(54) METHOD AND SYSTEM FOR SIMULATING SURGICAL PROCEDURES

(71) Applicant: Surgical Theater LLC, Elyria, OH (US)

(72) Inventor: Mordechai Avisar, Euclid, OH (US)

(73) Assignee: Surgical Theater LLC, Elyria, OH (US)

( * ) Notice: Subject to any disclaimer, the term of this patent is extended or adjusted under 35 U.S.C. 154(b) by 0 days.

(21) Appl. No.: 13/651,549

(22) Filed: Oct. 15, 2012

(65) Prior Publication Data

US 2013/0047103 A1   Feb. 21, 2013

Related U.S. Application Data

(63) Continuation of application No. 12/907,285, filed on Oct. 19, 2010, now Pat. No. 8,311,791.

(60) Provisional application No. 61/252,761, filed on Oct. 19, 2009.

(51) Int. Cl.
   *G06F 7/00* (2006.01)
   *G06F 19/00* (2011.01)

(52) U.S. Cl.
   CPC ..................................... *G06F 19/00* (2013.01)
   USPC .................. 703/11; 702/19; 702/20; 707/700

(58) Field of Classification Search
   CPC ....................................................... G06F 19/00
   See application file for complete search history.

(56) References Cited

U.S. PATENT DOCUMENTS

| | | |
|---|---|---|
| 5,595,703 A | 1/1997 | Swaelens et al. |
| 5,768,134 A | 6/1998 | Swaelens et al. |
| 5,826,206 A | 10/1998 | Nemeth |
| 6,857,878 B1 | 2/2005 | Chosack et al. |
| 6,863,536 B1 | 3/2005 | Fisher et al. |
| 6,939,138 B2 | 9/2005 | Chosack et al. |
| 7,101,383 B1 | 9/2006 | Van Ess |
| 7,261,565 B2 | 8/2007 | Chosack et al. |
| 7,616,730 B2 | 11/2009 | Flohr |
| 2002/0059284 A1 | 5/2002 | Bronstein et al. |
| 2004/0253572 A1 | 12/2004 | Chosack et al. |
| 2005/0032028 A1 | 2/2005 | Chosack et al. |
| 2006/0036167 A1 | 2/2006 | Shina |
| 2007/0134637 A1 | 6/2007 | Bronstein et al. |
| 2009/0018808 A1 | 1/2009 | Bronstein et al. |
| 2009/0187393 A1 | 7/2009 | Van Lierde et al. |
| 2010/0009314 A1 | 1/2010 | Tardieu et al. |
| 2010/0092904 A1 | 4/2010 | Esposti et al. |
| 2010/0161076 A1 | 6/2010 | Pallari |
| 2010/0178644 A1 | 7/2010 | Meglan et al. |
| 2010/0191088 A1 | 7/2010 | Anderson et al. |

OTHER PUBLICATIONS

Montgomery, K. et al. Studies in Health Techology and Informatics, 2002, vol. 85, pp. 296-303.

*Primary Examiner* — Mary Zeman
(74) *Attorney, Agent, or Firm* — Pearne & Gordon LLP

(57) ABSTRACT

A system and method for converting static/still medical images of a particular patient into dynamic and interactive images interacting with medical tools including medical devices by coupling a model of tissue dynamics and tool characteristics to the patient specific imagery for simulating a medical procedure in an accurate and dynamic manner.

25 Claims, 16 Drawing Sheets

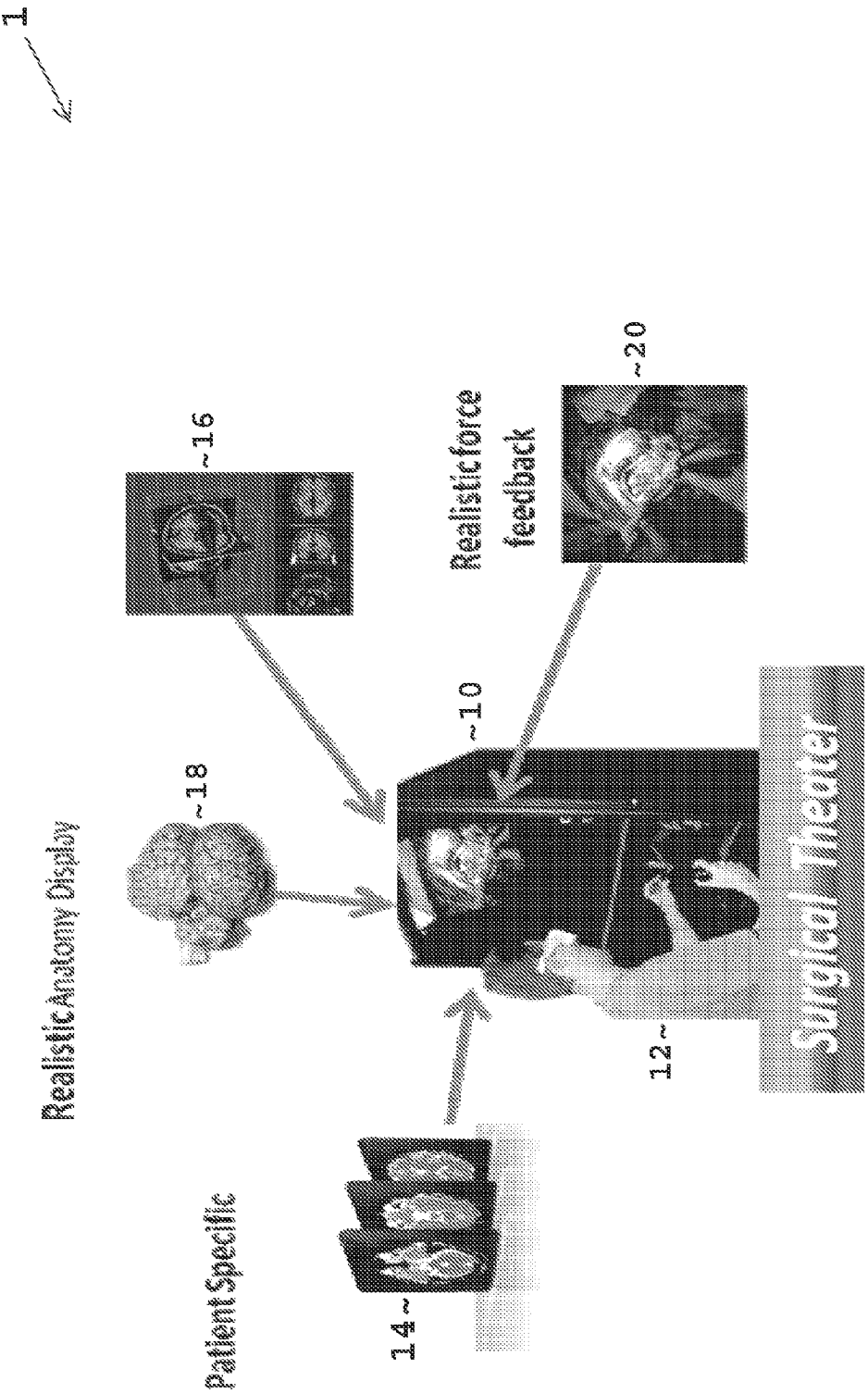

Architecture and workflow of SRP.

METHOD AND SYSTEM FOR SIMULATING SURGICAL PROCEDURES

CROSS-REFERENCES TO RELATED APPLICATIONS

This application is a continuation of application Ser. No. 12/907,285 filed on Oct. 19, 2010, incorporated herein by reference, which claims the benefit of U.S. Provisional Application Ser. No. 61/252,761 which was filed on Oct. 19, 2009 and is also incorporated herein by reference.

BACKGROUND OF THE INVENTION

This application relates generally to a system and method for simulating surgical procedures. More specifically, this application relates to a system and method for converting static/still medical images into dynamic and interactive images interacting with medical tools (such as, e.g., surgical tools, probes, and/or implantable medical devices) by coupling a model of tissue dynamics to patient specific imagery.

"Medical errors kill as many as 98,000 people annually at a total national cost of between $37 to $50 billion for adverse events and between $17 to $29 billion for preventable adverse events." "Surgical errors are the leading medical error" Source: *To Err Is Human: Building a Safer Health System, Institute of Medicine*. National Academy of Sciences. (1999).

During the course of high risk surgeries, such as, cerebral aneurysm repair surgeries, for example, the absolute orientation of the brain tissues is significantly altered as a surgeon pushes and cuts tissues to approach the aneurysm area. Therefore, the current utilization of the advanced surgery preparation and aiding systems such as Image Guided and Navigation Systems which are based on pre-registered 3D imageries, are limited in assisting the surgeons. Also, surgeries, such as aneurysm repair, are extremely time-sensitive, for example, due to various procedures including temporary vessel clamping to the aneurysm area. Therefore, the efficiency of the procedure is highly critical and detailed planning based on the patient specific local geometry and physical properties of the aneurysm are fundamental. To achieve a new level of pre-surgery preparation, 3D CT and MRI images are being increasingly utilized. However, those images offer only minor benefits, standing alone, for surgery rehearsal.

Surgeons lack a rehearsal and preparation tool that would provide them with a realistic visual model with physical tissue properties. Most importantly, it is desired to have a "full immersion" surgical tool that encompasses: (i) realistic "life-like" 3D display of the patient-specific area of surgery (for example—aneurysm); (ii) modeling of the local patient-specific area of surgery geometry and physical properties; (iii) interface enabling manipulation of the patient-specific area of surgery model and virtually perform surgical actions such as cutting, shifting and clamping; and (iv) interface to provide feedback cues to the surgeon.

SUMMARY OF THE INVENTION

The disclosed system and method, call the "Surgical Theater" provides a platform that convents static/still medical images into dynamic and interactive images by coupling a model of a specific tissue's dynamic attributes to patient specific imagery. This dynamic and interactive image/model creates a new novel and original standard for medical imagery and has many applications.

The Surgical Theater design facilitates a unique and exclusive ability for premier fidelity, fine cues and computing capabilities that handles large volume of information under 'hard real time constraints' while maintaining a real time performance and accuracy in a similar manner as in the unrelated field of Flight Simulation technology. Networking of several PCs such that each one of them is dedicated to handle one segment of the simulated scenario, those segments may include: visual, dynamic and modeling, user interface and so on. Allocation of a separate PC for each one of the system's sub segments allows extreme simulation fidelity by dedicating large computing power to each one of the system segments. The architecture provides the system components that enable all the sub systems to work as one system under hard real time constrains, such that time lag and latency are minimized for the creation of the realistic and immersive scenario.

Of course, alternative arrangements are possible, including the use of mainframes, or the use of multiple PCs for each segment, if necessary. Multiprocessor computers can be utilized to improve performance, and a specialized computer having a large number of processors operating in parallel might be utilized, rather than networked computers, in some instances.

Provided are a plurality of embodiments of the invention, including, but not limited to, a method of connecting and synchronizing the separated nodes of the said network by a management program that sample and updates each one of the nodes with the relevant changes and status of the others nodes, Also provided is a real time algorithm that analyzes the samples, and determine the rate, resolution and range and scope of the updated information between the network nodes, resulted with optimization of the network traffic and efficiency of bandwidth Also provided is an algorithm that analyzes the implementation of duplicated models in multiple for parallel computing for improving the modeling fidelity while minimizing the network traffic and bandwidth Further provided is an algorithm setting dynamic thresholds for the changes of the models (for example, the total volume change of tissue extraction or movement and change of location of a vessels) and, therefore, allowing distribution (among the peers) only of the changes that exceeded the predetermined thresholds, resulting in an increased efficiency of the network traffic load. This algorithm allows performing the models calculation in high resolution and accuracy, yet, also setting a threshold for publishing updated results of those calculations only when the resulted calculation at time T accessed the threshold differences comparing to time T−1

Still further provided is an algorithm that labels the distributed messages that each peer transmits to the network that allows all the peers to pre-determine whether the information in the transmitted message is relevant to the listening peer at a given time.

Also provided is a modeling system for performing a surgical simulation, comprising: a database for storing patient medical images of one or more organs of a particular patient with the database also for storing standard characteristics of the one or more organs; an image generator for generating a dynamic image of the one or more organs by utilizing the patient medical images of the one or more organs in combination with the characteristics of the one or more organs to create realistic dynamic images of the one or more organs representing the one or more organs of the particular patient; a user tool generator for generating a tool model of a user tool (e.g., a surgical tool, probe, implantable medical device, etc.) for dynamically interacting with the realistic dynamic images; a user input interface for accepting inputs from a user, the inputs for dynamically manipulating the user tool image for the dynamic interacting with the realistic dynamic images for simulating a medical procedure, such that the tool model is utilized by the image generator for generating an image of the tool image dynamically interacting with the realistic dynamic images based on the characteristics and the inputs for realistically simulating the medical procedure; and a display for displaying, to a user, the simulated medical procedure including showing the user tool image dynamically interacting with the realistic dynamic images of the one or more organs.

Further provided is a method for simulating a medical procedure, comprising the steps of:
  storing patient medical images of one or more organs of a particular patient;
  storing standard physical properties of the one or more organs;
  generating a three-dimensional dynamic image of the one or more organs by utilizing the patient medial images of the one or more organs in combination with the characteristics of the one or more organs to create realistic dynamic images of the one or more organs representing the one or more organs of the particular patient;
  generating a three-dimensional model of a user tool for dynamically interacting with the realistic dynamic images;
  accepting instructions from a user, the instructions for dynamically manipulating the user tool image for the dynamic interacting with the realistic dynamic images for simulating a medical procedure and for providing realistic feedback to the user representing the interactions between the tool image and the realistic dynamic images in a manner similar to a corresponding medical procedure on a real patient, such that an image of the tool image is generated dynamically interacting with the realistic dynamic images based on the physical properties and the inputs for realistically simulating the medical procedure in a manner corresponding to the medical procedure performed on the real patient; and
  presenting, to a user, the simulated medical procedure including showing the user tool image dynamically interacting with the realistic dynamic images of the one or more organs.

Also provided are additional embodiments of the invention, some, but not all of which, are described hereinbelow in more detail as example embodiments.

BRIEF DESCRIPTION OF THE DRAWINGS

The features and advantages of the examples of the present invention described herein will become apparent to those skilled in the art to which the present invention relates upon reading the following description, with reference to the accompanying drawings, in which:

FIG. 1 provides a high-level schematic of an example embodiment;

DETAILED DESCRIPTION OF THE EXAMPLE EMBODIMENTS

Figure 1A:
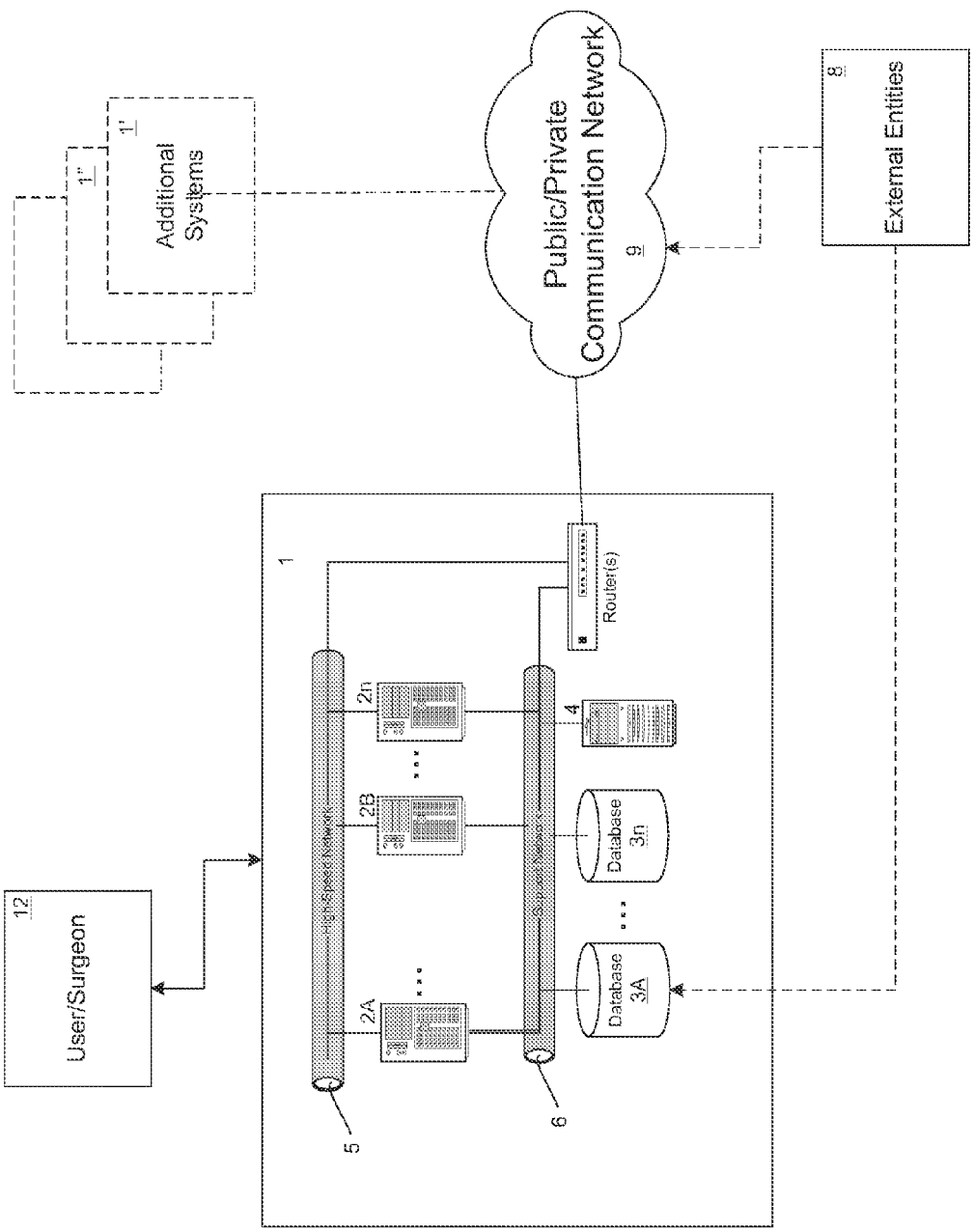
FIG. 1A provides another high-level schematic of a hardware implementation of the example embodiment.

The disclosed system and method (hereinafter "Surgical Theater"), is provided by a computerized system that convents medical images into dynamic and interactive images by coupling a model of a specific tissue's dynamic attributes to patient specific imagery. This dynamic and interactive image/model creates a new, novel, and original standard for medical imagery and has many applications. Among others, the system/method can be utilized by medical imagery navigation systems and image guided and robotic surgery systems that can enhance their planning performances by utilization of Surgical Theater dynamic and interactive tissue models coupled with the patient specific imagery.

One of the example applications is a Surgery Rehearsal Platform (SRP) that equips surgeons with a patient-specific surgery rehearsal system that is tailor-made to patients' own anatomy. The Surgical Theater address challenges in surgeries that involve high-risk activities, such as heart and brain surgeries including valve repair and replacement, bypass surgeries, brain tumor removal, Aneurysm clipping, and others.

For example, in the case of open/classic brain surgeries, such as brain tumor and brain aneurysm, for example, the Surgical Theater converts CT and MRI images and creates a realistic three dimensional (3-D) model of the brain tumor or aneurysm area with a dynamic modeling of the organisms, including the tumor, along with the surrounding tissue and blood vessels. The system is connected to life-like surgery tools, responding to actions taken by the surgeon, helping him/her to better prepare for the surgery. The Surgical Theater system simulates realistic events such as brain swelling, damage to blood vessels, brain tissue shifting during an operation blocking access to the remaining parts of the tumor, among others. The system can be used as a planning and preparation tool, allowing surgeons to tailor a specific surgical strategy for a given case, maximizing the surgery efficiency while minimizing the risk.

The following example focuses on Surgery Rehearsal Platform (SRP) application for cerebral aneurysm clipping surgery. The aneurysm SRP converts patient specific medical imagery (e.g., from CT scans) and creates a realistic 3D model that includes: a model of a patient specific surgery area (e.g., a cerebral aneurysm); a dynamic modeling of the surrounding organisms, such as the blood vessels and the surrounding tissue; and life-like surgery tools and commercial aneurysm clips. The modeling and integration of commercial tools provides a risk-free environment in which the surgeon can iteratively develop, rehearse and refine the surgery strategy, making advanced critical choices, for example; the optimal orientation of the head and the approach to the aneurysm, pre-selections of commercially available aneurysm clip(s), and responses to adverse occurrences specific to a patient's case. The vital insights gained during this rehearsal experience will provide the following examples of clinical benefits for the patient, the surgeon, and the hospital: (i) Reduced potential for intra-operative adverse events or complications, (ii) Improved surgeon's insight for successful response to adverse events, (iii) Decreased operative time. The surgeon's insights from this type of rehearsal experience will minimize the chance of premature aneurysm rupture and minimize the time needed for dissection and clipping while using temporary vessel occlusion, thereby reducing surgery risks and enhancing the likelihood of a successful surgery outcome. Modeling of experimental tools allows the surgeon or the tools manufacturer to develop new tools and new surgical approaches based on real life patient cases.

Aneurysm repair is one example of clinical need where time-efficiency of the procedure is highly critical and detailed planning based on the local patient specific geometry and physical properties are fundamental. Use of the system can result in an enhanced clinical outcome and a better operational efficiency.

Additional clinical needs that have been indentified that could benefit from these techniques include, for example: matching the optimal heart valve for the patient's own anatomy before the surgery, and optimal removal of a damaged section of an aortic aneurysm and replacing it with a graft. The SRP address opportunities in the area of complex open/classic surgeries procedures such as brain and heart surgeries; including brain aneurysm repair, heart valve repair and replacement, aortic aneurysm, bypass, and others. This surgeries market encapsulates more than 500,000 surgeries performed annually in approximately 3000 surgery centers in the United States.

The Surgical Theater line of products can include a software package for Image Guided systems. Such a product provides enhanced accuracy and performance for such systems. As the anatomy of the pre-registered imagery that those system use changes in the course of the surgery, the performance of those systems can be significantly enhanced through use of the Surgical Theater dynamic and interactive tissue models without additional radiation to the patient and with less interruption to the procedure by additional scans.

Surgical Theater can be utilized to provide a national connected-health platform to support a Collaborative Theater through the use of a plurality of SRPs at different hospitals.

Typical Scenario of Operation and System Overview

FIG. 1 provides an example embodiment for one application of the system 1 where a patient specific scan image (CT, MRI or similar) (14) is fed to the system's console (10), an algorithm that creates a 3 dimensional realistic anatomy display (18) adds texture, shadow, shadowing and other cues to the image, a mechanical properties algorithm (16) assigns mechanical behavior characteristics to the image and transfer the image from static/still image to a dynamic and interactive image/model. Interfaces with or without force feedback (20) are connected to the system allowing the surgeon/operator (12) to manipulate the image/model that the system creates; the surgeon can select tools and implants from libraries of tools and implants including characteristics of those tools and implants. The surgeon then performs a virtual surgery on a manipulateable, dynamic and interactive 3 dimensional image/model of his patient organism in a realistic and dynamic manner.

The system includes an executive program that runs and manages all the system components and updates the status of the sub components according to the surgeon/operator (12) actions. For example, when the surgeon uses the interface (20) to push a tissue (such as by using a chose tool) that he sees in the display (18), the mechanical properties model (16) receives the information regarding the force that was applied, e.g., the direction of force; the tool that is being used including its material and shape and other mechanical characteristics of the tool, then the mechanical properties are used to calculate a new state of the 3 dimensional orientation an ad setup of the image according the force that was applied, the executive program send the calculated 3 dimensional matrix to the realistic anatomy display (18) that was created by the mechanical properties algorithm (16), the realistic anatomy display calculates the new image and its cues due to the change of image e.g., a new set of shadows and shadowing due to the new orientation of the image components are determined. Simultaneously, the mechanical properties model (16) send a set of parameters to the force feedback interface (20), these parameters include information of the force that the surgeon/operator (12) needs to sense due to the interaction with the organs (the force that the organ returns after the surgeon pushes or otherwise interacts with the tissues). This process of calculation of new stage at each one of the system's components (14, 16, 18, 20) is executed rapidly and continuously in cyclic manner, and each cycle is completed within a frame time of milliseconds, allowing the surgeon/operator to receive real-time and realistic cues and real-time reactions to his actions.

The Surgical Theater is a system, as shown in FIG. 1A, that integrates several computers (PCs) 2A-2$n$, one or more databases 3A-3$n$ and other hardware components (e.g., networks 5, 6) and proprietary software into one complete system 1 (see both FIGS. 1 and 1A) that is structured into an immersive chamber/console sized about as big as a small walk in closet (see console 10 in FIG. 1). Once the surgeon 12 starts the system, the surgeon loads the set-up parameters of his patients which include details of the patient to allow the system to up-load the relevant data, the Surgical Theater than loads all the patient's available CT and MRI images from a patient images 14 into the database(s) 3 and other information that concern the simulated models such as patient age, gender and so on (some or all of which may be obtained from external entities 8, such as medical databases, for example). The system utilizes tissue information parameters 16 from a system database. The system 1 performs a segmentation process and indentified the Entities of the organ, Entities are vessels, tissue, tumor, and so on to create the simulated image model 18 shown to the surgeon on the display of the device. The system provides realistic tactical feedback 20 via feedback mechanisms to add further realism to the simulation.

The system applies the layers of the realistic visual, the mechanical properties and other relevant parameters 16 from the system database(s) and characteristics relevant to the case, all applied on the top of the CT and MRI images 14 from the patient images database(s) 3 and synchronized with those images. The synchronization creates, for example, vessel mechanical properties that are 'clamped' or 'attached' to the vessel images and so on to provide realistic simulation capability. The surgeon can be provided the ability to "fine tune" the models and adjust the mechanical properties of a certain area of the organ. For example, the surgeon may adjust the elasticity and other mechanical characteristics of the Entities behavior.

Subsequently, after such a set-up, the Surgical Theater projects the 3 dimensional organ model 18 presented in a realistic visual fidelity with realistic features such as; texture, shadowing and other features that adds realism to the simulated image. Each segment of the visual model 18 is coordinated and corresponds with an appropriate mechanical properties model from the system database 16 and other relevant properties of the specific case.

At this stage, the system allows the surgeon to browse and chooses from the system's virtual libraries 16 in the system database the relevant surgery tools and other elements (in the system software terms those tools and elements are "Entities" as well) that he may need to perform the surgery (or other procedure). Such elements may include; seizers and clamps, clips for aneurysm, artificial heart valves, and other elements appropriate for the specific case. (Adding additional systems 1', 1" . . . connected to the system 1 via a network 9—such as over the Internet or a private network—can result in a collaborative theater platform, described in more detail later in this disclosure.)

All of the various Entities are represented by the system in high-fidelity distributed models and functioning in a distributed architecture, e.g., each Entity typically has a separate subEntity, where the subEntity is, for example, a "visual entity" or "mechanical entity" and so on. Each subEntity exists in one of the different environments (e.g., the visual system environment, the mechanical modeling environment and so on, described in more detail below) distributed among a plurality of computers. Each such subEntity is responsible for its own performance (i.e. presenting the realistic visual of the Entity, or performing the Entity's mechanical operation, for example).

The subEntities communicate via a distributed network (described in more detail below) to synchronize and coordinate the subEntities into a one integrated Entity compound model. For example, when a tissue is being pressed by a surgery tool, the surgery tool pressure characteristics (e.g., the location, orientation and amount of pressure and so on) is distributed via the network, each one of the subEntities is responsible for 'listening' and concluding if it is being affected by this surgery toll pressure; once a subEntity determines that it is being affected, each such subEntity (for example, tissue Entity) models the affect on their subEntity model, e.g., the visual subEntity, presents the visual effects (such as bloodiness of the tissue), and the mechanical properties models the shift of the tissue. Each subEntity distributes the change—for example, the tissue location and dimension changes—over the network so the other subEntities will be able to determine if they are being affected by this change. At the end of such action, all the subEntities of the tissue for the above example, (and the other Entities), become accustomed to, and, if needed, adapt their states and the models to, the new action that was sourced and initiated, in the above example, by the surgery tool.

Thus, the various functions (subEntities) can be distributed among various computers connected in a peer-to-peer network utilizing distributed data and state duplication (for keeping local copies of the state of the simulation), all listening on the network for any action that impacts their portion of the simulation, in which case they update their parameters via the network to keep the system accurate, which may, of course, impact other functions in other subEntities, which will therefore catch that fact by their monitoring of the network, leading to further updates, and so on. In this way, the system distributes the functionality among many computers in a parallel fashion so that updating can occur much quicker than it could if only a single computer were used. Only those subEntities impacted by a change need respond, and thus network traffic can be reduced to essentials.

The Surgical Theater allows the surgeon to record his actions and save them for later playback, to demonstrate his surgery plan to the chief surgeon or resident, or, to share information with other surgeons, demonstrate new techniques he is working on, practice the surgery, and so on. The system's interfaces to the surgeon include surgery interfaces (e.g., seizers handles) that include force feedback that is delivered to those tools to allow the surgeon to sense the force feedback cue of his actions, realistically simulating an actual procedure.

Once the surgery tools and the other Entities are selected by the surgeon, they are integrated into the virtual surgery scene and turn into an integrated element of the simulated scenario including realistic visuals features and mechanical properties and operation properties features that are applied to each one of those selected items. For example, the simulated scissors reflect mechanical characteristics of real scissors and will cut in the simulation as the real scissors do; and, aneurysm clips, when placed at the simulated vessel, simulates blocking the blood flow.

Next, the surgeon performs the surgery actions at any stage of the virtual surgery; the surgeon can "freeze" the simulation and rotate the organ to observe the area of his interest from different orientations and perspectives. The surgeon can "mark point of time" of the virtual surgery and can command a "return to the mark point". For example, the surgeon can mark the time before clamping an aneurysm and return to this point of time while "un-doing" all the actions that took place after this point of time. In this fashion, the surgeon can evaluate different surgery approaches of a selected phase of the surgery without restarting the entire surgery from the original starting point. Several such 'mark points' are available allowing the surgeon to return and "re-do" actions and exams/rehearse on several selected phases of the surgery. Other scenarios of the Surgical Theater use may include:

- Surgeon rehearsals toward a surgery;
- Surgeon demonstration to the chief surgeon;
- Surgeon demonstration to a resident;
- Surgeon research and develop a new method;
- Resident practice;
- Platform for development, testing and validation of surgery equipment, tools, or equipment; for example: aneurysm clips, artificial heart valves and so on that will be provided in a realistic simulated environment;
- Surgeon community platform to share knowledge and accrued experience;
- Platform for resident and surgeon evaluation exams and certification;
- Platform to promote the use of specific surgical tool or instrument such as artificial heart valve or aneurysm clip;
- Practicing on time of crucial phase of the surgery;
- Prior selection of aneurysm clips before even entering the operating room (OR);
- Prior plan of optimal approach to the aneurysm feeding vessels;
- Plan the optimal placement and orientation of the aneurysm clip to maximize the exclusion of the aneurysms from the cerebral circulation while minimizing the stress on the surrounding vessels;
- Reduced possibility for adverse events;
- Matching the optimal heart valve for the patient own anatomy;
- Optimal removal of the damaged section of the aortic aneurysm and replacing it with a synthetic tube (graft); and
- Enhanced accuracy and better performance for Image Guided and Robot Assisted Surgery systems without additional radiation to the patient and less interruption to the procedure.

Collaborative Theater

Figure 2:
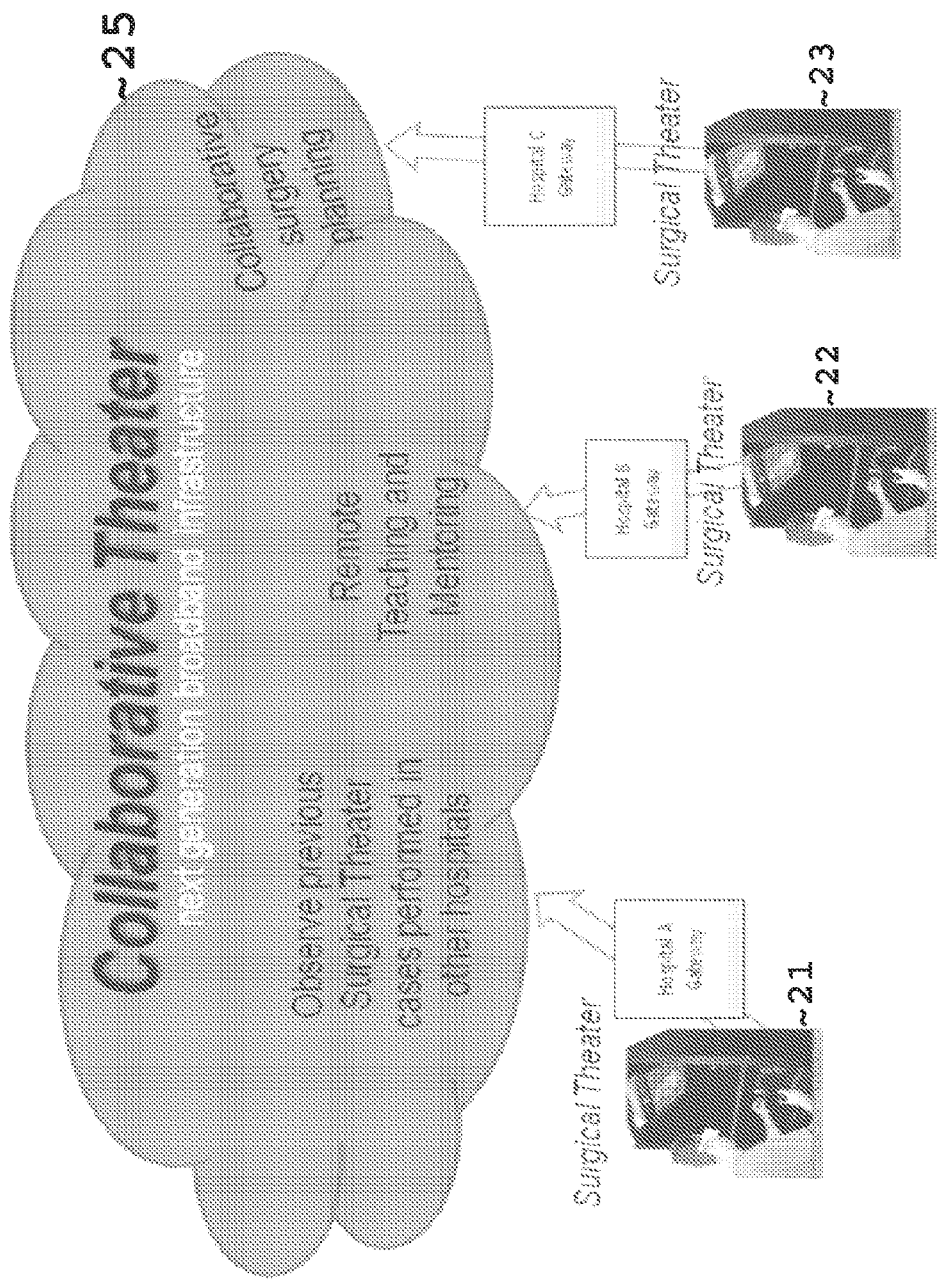
FIG. 2 a high-level schematic of an example of the Collaborative Theater concept.

FIG. 2 shows a high-level example implementation of the Collaborative Theater concept. By leveraging next generation broadband infrastructure 25, individuals using SRPs 21, 22, 23 . . . from different hospitals will be connected allowing surgeons across the nation and across the globe to collaboratively plan a surgery case, e.g., surgeons from two or more distributed sites step into their SRP and rehearse, together, on a patient case toward a surgery. This Collaborative Theater allows surgeons to study the best practice methods by observing previous Surgical Theater cases as well as providing remote teaching and mentoring. The Collaborative Theater allows all the hospitals that are connected and using the SRP to gain access to the up to date accrued knowledge and most recent "best practices".

System Level Design

The system level design description is outlined in the preceding sections. The visual rendering engines analyze 3D MRI and CT patient-specific images and create computerized segmented modules that represent the anatomical structures and features of the particular image. The medical market has a vast number of advanced Digital Imaging and Communication in Medicine—DICOM (1) viewers. Their feature sets range from layered black and white slices in 3 different panels that could be cross-referenced to a complete ability to fly through static subsets of 3D images of patient's organs. In addition, there are 4D and 5D features that record various functional and dynamic changes of organs in a form of a movie clip. As magnificent as those captured images or moving sequences might be, they are a fixed set of snapshots images in time.

The Surgical Theater takes existing 3D conversion processes and adds the features specific to the human tissues and structures based on physical and mechanical properties that are then stored in the system database. Once this patient-based model is set in motion in the virtual world, the Surgical Theater introduces a set of virtual surgical tools that allow the surgeon to manipulate (push, cut, clamp, etc) those models similar to real surgery tissue manipulation, providing an intuitive experience for the surgeon.

Figure 3:
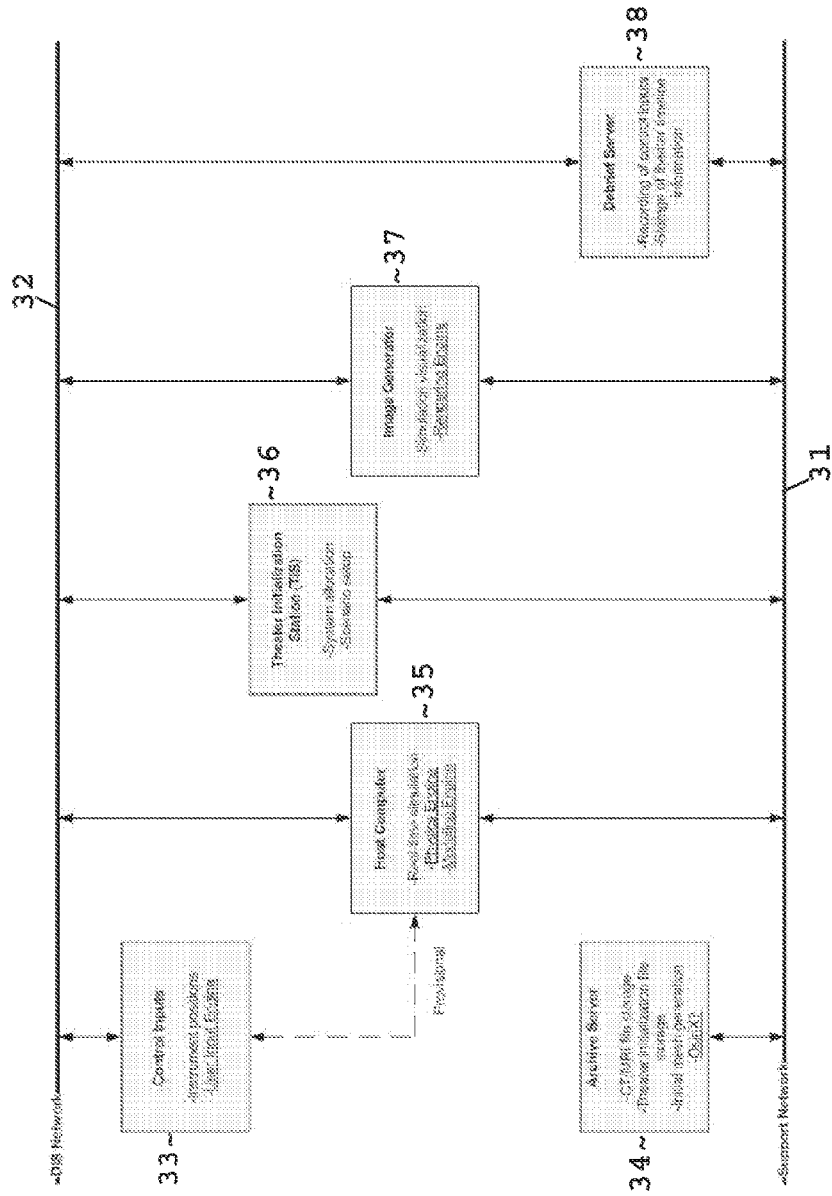
FIG. 3 shows an example breakdown of a distributed simulation network concept for the example embodiments.

FIG. 3 provides a breakdown of an example Surgical Theater distributed simulation network (Surgical Theater DIS (ST-DIS) is presented). Each of the components (i.e., blocks) in the figure is an isolated computation station (that can be executed on a stand-alone computer or collection of computers) with a designated set of functions. The stations are appropriately connected with a regular support network 31 (such as an Ethernet network, for example) that handles slow irregular traffic, like transferring of vast amounts of DICOM data. Upon more intense data processing demand, the stations are supported by a specialized Distributed Interactive Simulation (ST-DIS) Network 32 that is a hardware isolated network used only for high priority simulation data (which can be implemented in high-bandwidth Ethernet, for example). The ST-DIS Network 32 carries volatile simulation information and allows for such an exquisite simulation load distribution.

The Surgical Theater's ST-DIS is a network architecture for building large-scale virtual worlds from a set of independent simulator nodes. The simulator nodes 33-38 are linked by the networks and communicate via a common network protocol (such as TCP/IP, for example). The ST-DIS infrastructure enables various simulators to interoperate in a time and space coherent environment. In the Surgical Theater's ST-DIS ST-DIS system, the virtual world is modeled as a set of "Entities" that interact with each other by means of events that they cause. The simulator nodes 33-38 each independently simulate the activities of one or more of the Entities in the virtual world of the simulation and report their attributes and actions of interest to other simulator nodes via messages on the network. The other simulator nodes on the network are responsible for "listening" to the network messages, determining which ones are of interest to them (based on the Entities they are simulating) and responding appropriately.

One of the features of the ST-DIS network and simulation architecture concerning distributed interactive simulation is that there need be no central server or processor. Each simulation application maintains its own copy of a common virtual environment in its own memory or database. Representations of this environment are distributed by various means to all simulation applications prior to any real time operation. ST-DIS is basically a peer-to-peer architecture, in which data is transmitted available to all simulators where it can be rejected or accepted depending on the receivers' needs. By eliminating a central server through which all messages pass, ST-DIS reduces the time lag for a simulator to send important information to another simulator. This time lag, known as latency, can seriously reduce the realism, and therefore the effectiveness, of a networked simulator. Effective distributed simulation depends on very low latency between the time that a new state/event occurs for a simulated entity to the time that the state/event is perceived by another entity that must react to it. Any delay introduced by the training device could result in negative reinforcement to the trainee.

Referring again to FIG. 3, the Archive Server 34 is generally used to perform the tasks of downloading and retaining in a database large amounts of data necessary for simulation. In addition, the Archive Server 34 can be used to prepare obtained data for further use in the simulation. Note that because its duties are typically global in nature, and not critical to the simulation activity, the Archive Server 34 is typically only connected to the support network 31.

FIG. 3 is a network architecture that includes a off line "support" network (31) that "Archive Server" (34) that loads the medical images (CT/MRI) and additional initialization data stored in a database (for example, the patient name, age and so on and files to be included in the scenarios such as surgery tools libraries) "Debrief Server" (38) that records control inputs and store the scenarios and all the actions in a timeline information and allows playback of scenarios and actions. The real time network (32) is the network that transfers messages between the systems node during the simulation in a real time fusion-one way for implementing this network can be a Distributed Interactive Simulation (DIS) network (32), the components that connected to this network are; Control Input (33) that connected to the surgeon/operator systems interfaces, this node has an optional direct physical connection to the Host Computer (35) that may be implemented in a case that the real time requirements of the system cannot be satisfied by the DSI network and a direct physical connection between those node sis needed. The Host Computer (35) includes the executive manger program and other models and simulation components and it is responsible for the real time synchronization and timing of the entire systems.

The Theaters Initialization Systems (TIS) (36) performs that system allocation and setup for each one of the nodes, for example, when the surgeon select a specific tool to use, the TIS allocates/activates the appropriate models of this tool for generating an accurate tool simulation (with tool characteristics stored in a database) for all the nodes assuring that all the nodes are set up with the same initialization. The Image Generator (36) performs the rendering and visualization tasks of the scenarios. The Host Computer (35), the TIS (36), the Image Generator (36) and the Debrief Server receive and exchange information with off line for initialization from the Support network (31) and receive and exchange information with the real time network (32) for "on line" and real time simulation.

Needed organ surface and volume data are extracted from an existing MRI/CT scan stored in the database. To obtain 3D organ surface data, the system can use a DICOM viewer and data management system such as the OsiriX (or comparable) that is open source software implemented for Apple Macintosh computers, for example. By "tapping into" OsiriX's ability to generate 3D surfaces of organs and organ groups based on the voxel density values with Objective C source code, the Surgical Theater adds an ability to store information about the 3D surfaces and organ types that describe into a flat file in a database. The entire set of parts of this study stored in this manner in the system database so that it is later transferred to the Image Generator Station 37 that recreates the patient-specific images based on standard characteristics of the organs. Once the necessary rendering data is obtained, the rendering platform for Image Generator Station 37 is applied to the image. For this, a proprietary Image Generator algorithm is integrated (such as a Flight IG; see the features in the separate headings for the Realistic Image Generator—RIG) with a Visualization Tool Kit.

The IG has unique features that deliver fine cues such as shadowing, texture, and material properties that are assigned to the visual models and as further detailed in the RIG sections. Not only does the IG create realistic and fully immersed environments by using those features, it can also process large volume of visual data base models under hard real time constraints. Enabled by the combination of the DIS architecture and the "Entity" design, the network traffic is minimized and the anatomy of the peer-to-peer nodes create a highly efficient real time system.

After the patient-specific images have been successfully rendered, various physics libraries are added in order to create proper simulation. Pushing and manipulation of the brain tissue is simulated using extensive research embodied in modeling platforms such as the OpenTissue (or comparable) collections of libraries that are available. The OpenTissue, for example, is an open source collection of libraries that models volumetric shells and other complex behavior of 3-dimensional shapes. Customized libraries can also be developed for use. Specificity of the brain tissue physics and mechanics properties that derived from the research of mechanical properties of brain tissue in tension can be utilized, for example. Experimental papers are available that provide mathematical models of the mechanical manipulation of animal brain samples. Dynamic and realistic interaction of simulated surgical tools with the simulated tissues are implemented in the algorithms and approaches as described by Viet HQH, Kamada T, and Tanaka H T, *An algorithm for cutting 3D surface meshes and/or volumetric models*, 18th International Conference on Pattern Recognition, 4, 762-765. 2006 (incorporated herein by reference). The work looks at various tools and tissue types to create a realistic simulation specifically for implementation of surgical simulations.

The software code of the example Surgical Theater is written in a commercial environment such as C++, with the code being designed to run in windows operating system, a Linux system, or compatible. In the coding development process, emphasis is given for the code real time execution and code efficiency all aimed to maintain a real time system performance while minimizing the latencies.

The visual system driver located in the Image Generator (37) is designed with an optimizers environment, such as OpenGL or similar, enables high-performance rendering and interaction with large models while maintaining the high model fidelity demanded, providing attention to detail while maintaining high performance in a cross-platform environment.

For computing efficiency purposes, each of the visual model's Entities have several Level of Details (LOD) representations; high LOD is presented in areas of the simulation scene in which the surgeon needs high resolution at, and, lower LOD is presented in areas of the simulation scene in which the surgeon has no immediate interest or interaction with. For example, tissue visual model is presented in high LOD in the area around the surgeon interaction and with lower LOD in areas that the surgeon doesn't have immediate interaction with. The LOD can be dynamically adapted: a surgeon's actions such as pointing the surgery instruments toward a specific area can be utilized by the LOD optimization algorithm for the dynamic allocation of the LOD for specific section of the visual models.

The typical system's computer is a PC with a multiple core which provides flexibility and growth potential. The computer system includes random access memory, Ethernet ports, system disk, and data disk.

For the validation of the Surgical Theater (image quality, realism, image controller and manipulation), the skills and experience of senior surgeons are utilized. The surgeons are used to evaluate the system by performing specific surgical procedure while comparing it against their vast neurosurgical experience as well as against a specific case that they have already operated and is being simulated in the Surgical Theater.

1. The Surgical Theater Block Diagram describes the functionality and the flow of the process (vs. the actual network connection of FIG. 3) from the row data of the scanted image DICOM 41 through the process of segmenting the row data (to indentify soft tissue, vessels and so on). Then the Image Generator assign visual representation of each segment (shadow texture and so on), this image is connected via the DIA 44 network to a projection interface 46 and to the Host 45 that will update the image generator 43 with the surgeon actions that are connected through the Surgeon Interface 47 and the mechanical Properties and other modeling that the Host includes that all will reflect the new state that the Host will send to the IG 43 during each simulation cycle.

Figure 4:
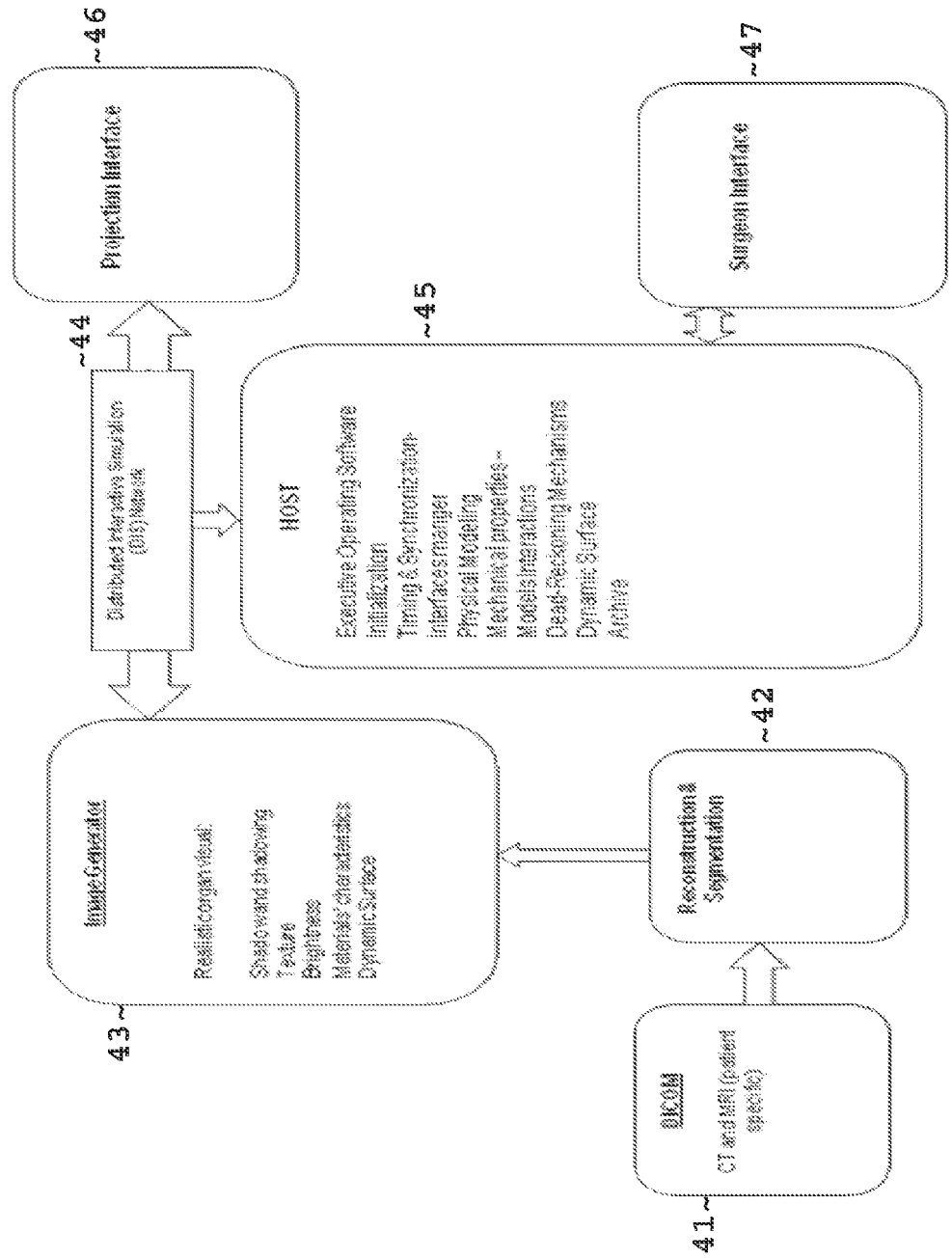
FIG. 4 is a block diagram block diagram showing design level and preliminary software design requirements.

FIG. 4 shows a block diagram providing the example system's block diagram design level and the preliminary software requirements.

DICOM CT and MRI 41—To obtain 3D organ surface data, a tool such as the OsiriX DICOM (or comparable) viewer and data management system as the baseline code;

Reconstruction & Segmentation CT and MRI 42—Object oriented source code that is adding ability to store information about the 3D surfaces and organ types that will describe the physiology in a flat file;

Image Generator (IG) 43—Integration of a proprietary Flight Simulation Image Generator with a Visualization Tool Kit (VTK) (or comparable); Flight Simulation Image Generator has features that deliver fine cues such as shadowing, texture, material properties that assigned to the visual models and others.

HOST 45—After the system had successfully rendered the patient-specific images of the potential surgical site, various physics libraries are formed in order to create a accurate simulation;

For the modeling baseline code utilized in the Host 45, OpenTissue (or comparable) can be used, which is an open source collection of libraries that models volumetric shells and other complex behavior of 3-dimensional shapes. Specificity of the brain tissue physics and mechanics is derived from the research of mechanical properties of brain tissue in tension. These experimental papers provide a mathematical model of the mechanical manipulation of animal brain samples. Interaction of surgical tools with the simulated tissues is implement the algorithms and approaches as described by Viet et al.; the work looks at various tools and tissue types to create a realistic simulation specifically for implementation of surgeries interfaces. The HOST computer performs additional tasks such as Executive Operating Software, Initialization, Timing & Synchronization, Interfaces manger, Physical Modeling, Mechanical properties, Models Interactions, Dead-Reckoning Mechanisms, Dynamic Surface and Archive, for example. Each of those sub systems in the HOST 45 are built in a way that they could be "spun out" to a separate PC within the DIS network; the interaction of the subsystem is based on the DIS architecture, allowing easy spin out. For example, the Physical Modeling and Mechanical properties are shown in the system diagram as an integrated part of the HOST, yet, once it is desired, for any reason (such as needing more demand for computation power than the HOST computer can provide) to allocate separate one or more PCs for the Physical Modeling and/or the Mechanical properties, this part of the code is being "immigrated" to a separate PC and from that peer PC communicates with the HOST and the other system's PCs, via the DIS while using the whole PC resources that they were installed at, while maintaining high real time coupled connectivity with the rest of the system via the DIS.

As used in the Host 45, "Physical Modeling" is the application of physics-based mathematical models to produce high-fidelity simulation of physical events, such as tissue cut and shifting. "Dynamic Surface" refers to the ability of simulation events and entities to alter the surface database in ways that are of importance to the simulation.

"Dead-Reckoning Mechanisms": the objective of dead-reckoning is to determine new states based on previous ones, i.e. by extrapolation. Only when the entity (i.e. vessel) true data differs enough from the extrapolated data (by a predetermined threshold) the new state is issued.

Distributed Interactive Simulation Network 44—The Surgical Theater Distributed Interactive Simulation (ST-DIS) is an architecture for building large-scale virtual worlds from a set of independent simulator nodes.

ST-DIS Characteristics:

Autonomy of Simulation Nodes: Each node is only responsible for the entity or entities it is simulating, and does not have to process what other nodes are interested in. Receiving simulations are responsible for determining the effects of an event on the entities it is simulating. The autonomy principle enables nodes to join or leave an exercise in progress without disrupting the simulation;

Transmission of "Ground Truth" Information: Each node transmits the absolute truth about the state of the entity/entities it simulates. The receiving nodes are solely responsible for determining whether their objects can perceive an event and whether they are affected by it. Degradation of information (essential for realistic description of system behavior) is performed by the receiving nodes;

Transmission of State Change Information Only: Simulations will only transmit changes in the behavior of the entities they represent, in order to reduce unnecessary information exchange;

Dead-Reckoning Mechanisms: The objective of dead-reckoning is to determine new states based on previous ones by using extrapolation. Only when the ground truth data differs enough from the extrapolated data (by a predetermined threshold) is a new state issued;

Simulation Time Constraints. Current DIS standards primarily support human-in-the-loop simulations. The simulation time constraints (100-300 milliseconds) were obtained based on human factors. Other types of simulations (such as war-games) operate faster or slower than real time;

Projection Interface 46—the interface for providing the simulation visual components to the surgeon utilizing a commercial high definition (and possibly even a 3D) display; and Surgeon Interface 47—the interface with which the surgeon interacts with the system, including the simulation surgical tools.

Experimental Design:

One of the features of the Distributed Interactive Simulation (ST-DIS) network and simulation architecture that concerns distributed interactive simulation, is that it is not necessary to use a central server or processor. Each simulation maintains its own copy of a common virtual environment in a local database. Representations of this environment are distributed by various means to all simulation applications prior to any real time operation. ST-DIS of this example embodiment is a peer-to-peer architecture, where all data is transmitted available to all simulators and is either rejected or accepted depending on the receivers' needs.

By eliminating the central server through which all messages pass, ST-DIS dramatically reduces the time lag for one simulator (computer) to send important information to another simulator (computer). This time lag, known as latency, can, if too large, seriously reduce the realism, and therefore the effectiveness, of a networked simulator. Effective distributed simulation depends on very low latency between the times a new state/event occurs for a simulated entity to the time the state/event is perceived by another entity that must react to it. Any delay introduced by the training device results in the negative reinforcement to the operator (e.g., the surgeon).

According to the recommended practice for communications architecture (IEEE 1278.2), the underlying communications structure should support 100 ms or less latency for packet exchange for closely coupled interactions between simulated entities in real-time (e.g. simulating high performance aircraft in a dogfight or simulating a surgeon performing brain surgery). This requirement is based on human reaction times that have been the basis of Human-In-The-Loop (HITL) flight simulator designs for many years.

Within the ST-DIS system, the virtual world is modeled as a set of Entities (as described previously) that interact with each other by means of events that they cause. An Entity is a sub-component in the simulated scenario, such as tissue, specific characteristics (such as—tissue mechanical properties,) creating a sub group of that "tissue entity". Another Entity can be a blood vessel, for example, and so on. Each Entity can have several subEntities that operate in a distributed manner (such as on different simulators/computers). Together, those subEntities are combined to create the complete Entity model. Those subEntities are, for example: the Visual subEntity that holds and simulates the Entity's visual feature and characteristics, or, the Mechanical Properties subEntity that holds and simulates the Entity's mechanical feature and characteristics. Each of those subEntities model code can run in a different computer (or group of computers) such as a PC, and they communicate with each other as well as with other Entities via the ST-DIS network. The simulator nodes, independently simulate the activities of one or more Entities (or subEntities) in the virtual world of the simulation and report their attributes and actions of interest to other simulator nodes via messages on the ST-DIS network. The other simulator nodes on the network are responsible for "listening" to the network messages, determining which ones are of interest to them (based on the entities they are simulating) and responding appropriately.

The above-described Surgical Theater architecture is based on this Distributed Simulation concept thereby enabling pioneer and exclusive abilities to deliver a premier fidelity which is an essential requirement for creating immersive scenarios crucial for the rehearsing of open/classic surgeries where the surgeon(s) interacts with the organ(s) by direct human sense. As each Entity is divided to its sub-components (visual, mechanical properties and so on), and as each of those sub-components/Entities' simulation code runs in a separate computer, this can maximize the computation power, and by that the creation of a unique and exclusive premier fidelity, fine cues, and computing capabilities while handling terabytes of information under hard "real-time" constraints while maintaining real time performance (e.g., less than 100 millisecond latency), the core capability of the Flight Simulation technology.

In an ST-DIS exercise, simulation entities communicate by exchanging messages via the network. These messages are known as Protocol Data Units (PDUs). The ST-DIS Application Protocol defined as the PDU, specifies both the format and data content, as well as the circumstances under which each PDU should be transmitted. There are 26 PDUs in the current version of the Application Protocol standard (the DIS protocol by that Institute for Simulation and Training 1994). The Aneurysm Surgical Theater is hereby presented as an example for the Surgical Theater's application that utilizes the ST-DIS. The initial list of the PDUs is listed in Table 1 with a brief description:

TABLE 1

Aneurysm Surgical Theater PDUs

| ENTITY EVENT | PDU CONTENT AND MEANING | PDU FREQUENCY |
| --- | --- | --- |
| Entity present location | Location, orientation and speed vector, and status of surgery tool and clip ('tools entities'), | approximately 5 times per second |
| Shift, Cut, Push | Location and orientation of action, width of action point of interactional and orientation of interaction | approximately 10 times per second |
| Modification of entity state | Differentiation change of Location, Orientation and other changed in relevant parameters (only) | Adaptive per the duration and extent of the change |
| Surgery tool moves through subdivision/ other section/organ | Location orientation and direction vector of the move | Adaptive per the duration and extent of the move |
| Cut in vessel | Location orientation and direction vector of the cut | Discrete, one time |
| Vessel building | Location orientation and direction vector of the building | Discrete, one time |
| Tissue extract/ shift/shrink | Location orientation and direction vector of the shift | Adaptive per the duration and extent of the move |

Table 2 is a sample of the system PDU list of the Surgical Theater.

TABLE 2

Surgical Theater-System PDUs

| PDU Type | Description |
| --- | --- |
| Entity Information/Interaction | an entity's state information |
| Entity State | a collision between two entities |
| Collision | |
| Interaction | |
| Cut | Surgery tool |
| Diffusion | impact or diffusing on an organ |
| Simulation Management | creation of a new entity |
| Create Entity | removal of an entity |
| Remove Entity | begin participating in the exercise |
| Start/Resume | leave a simulating state |
| Stop/Freeze | acknowledges receipt of certain |
| Acknowledge | SIMAN PDUs |
| Action Request | request specific action of entity |
| Action Response | acknowledge receipt of Action |
| Data Query | Response PDU |
| Set Data | requests data from an entity |
| Data | set or change certain parameters |
| Event Report | in an entity |
| Message | provide requested data |
| | occurrence of a significant event |
| | inputs a message into a data |
| | stream |
| Distributed/Regeneration | |
| Blood flow | active electromagnetic emissions |
| Pressed air | designation functions |

The following are the initial software and PDU definitions of the Aneurysm simulation. In real time distributed simulations, any data may be sent between applications; however, the following categories of data dominate and tend to tax network services:

Entity State—information which includes appearance, location, velocity, orientation, accelerations, and position/movement of articulated parts of simulated entities. Location and movement are dead reckoned and this packet is only sent to correct dead reckoned parameters. It may also be sent periodically as a heartbeat, or to compensate for lost packets. Radically maneuvering entities can transmit up to 15 packets per second. An average rate is 5 packets per second for a surgery tool;

Environment—temperature, moisture data is broken up into a series of packets to describe changes in the simulated environment. The update rate is relatively low, but the number of packets needed to represent complex patterns induces a significant network load;

Cut & Shift—packet pairs carry the information needed to describe the surgeon actions of cutting, pushing and the manipulation of the organ structure (i.e. tissues). The amount of information per packet is modest, and the total number of packets are limited to the number of actions the participants can perform, but surgeon actions tends to come in bursts, and those bursts can impact network performance; therefore, needing to be coded in efficiency and timed with consideration of the network load;

Autonomy of Simulation Nodes—Each node is only responsible for the entity or entities it is simulating, and does not have to process what other nodes are interested in. Receiving simulations are responsible for determining the effects of an event on the entities it is simulating. The autonomy principle enables nodes to join or leave an exercise in progress without disrupting the simulation;

Transmission of "Surface Truth" Information—Each node transmits the absolute truth about the state of the entity/ entities it simulates. The receiving nodes are solely responsible for determining whether their objects can perceive an event and whether they are affected by it. Degradation of information (essential for realistic description of system behavior) is performed by the receiving nodes; and Transmission of State Change Information Only—Simulations will only transmit changes in the behavior of the entities they represent, in order to reduce unnecessary information exchange.

In real-time simulations, the data listed above shares an important characteristic that is often overlooked when designing reliability mechanisms: the data is perishable and it becomes stale quickly. Most reliability mechanisms attempt to retransmit the original data to correct for packet loss. This approach may be useful for conventional applications (e.g. file transfer), but in distributed real-time simulation, such recovery is of little use. A better approach is a recovery mechanism that retransmits a fresh version of the data in a lost packet.

As outlined in the preceding sections, the Surgical Theater facilitated a visual rendering engine which analyzes 3D MRI and CT patient-specific images and creates computerized segmented modules that represents anatomical structures and features of the particular image. Medical market has a vast number of advanced DICOM viewers, but as magnificent as those captured images or moving sequences might be, they are based on a fixed set of snapshots in time. The Surgical Theater takes existing 3D model conversion algorithms and adds the features specific of the human tissues and strictures based on physical and mechanical properties creating a "living" image with models that reforms the patient specific CT/MRI images according to actions taken by the surgeon and based on the models that simulate the mechanical properties of each pixels in the image and realistic visual characteristics models. Once this patient-based model is set in motion in the virtual world, a set of virtual surgical tools are introduced allowing the surgeon to manipulate (push, cut and etc) those models similar to a real surgery tissue manipulation. Thus, the Surgical Theater provides an intuitive experience for the user.

For the Image Generator, the Surgical Theater of the example embodiment integrates a proprietary Flight Simulation Image Generator algorithm with a visualization code such as Visualization Tool Kit (VTK). As detailed in the following sections, the Surgical Theater Realistic Image Generator has features that deliver fine cues such as shadowing, texture, and material properties that are assigned to the visual models.

The Realistic Visual Sub System

This section focuses on the "realistic visual" segment of the Surgical Theater that is a modification of a Flight Simulation Image Generator that is capable of rendering satellite images into realistic 3 dimensional images and models that are converted into the Surgical Theater realistic Image Generator (RIG) handling and real time rendering CT/MRI DICOM images into a patients' specific realistic and dynamic CT/MRI images and models that are crucial for the open/classic surgeries where the surgeons interact with the organ by direct human sense.

The use of a visual system in the creation of the immersive simulation system in the field of Human factor Engineering is important; studies demonstrate that a high percentage of the immersion is constructed and contributed by the level of fidelity and realism of the visual system that the operator (e.g., pilot or surgeon) interacts with. Findings show that operators who rehearse on high fidelity visual systems completed the memory task including self-report of confidence and awareness states in significantly higher levels than the low fidelity group. A significant positive correlation between correct 'remember' and 'know' responses, and in confidence scores, are found when utilizing high fidelity, realistic simulation.

As outlined above, the Surgical Theater creates a realistic "life-like" digital rendition of the surgical site and the surrounding tissues/structures. Since this digital rendition is patient-specific and "life-like", it sets Surgical Theater apart from other simulators that use generic imagery to create approximate renditions of the surgical site, or, other system that simulates noninvasive procedures such as endoscopic, vascular and similar procedures, where the surgeon/operator interfaces the organism with a camera that has its own visual characteristics that are defined and limited by the camera specification and are very different from the visual characteristics of the bare and direct eyes view of the open/classic surgeon's where the surgeon interacts with the organism with direct sense of his eyes However, realistic "life-like" rendering presents a surmountable task due to the complexity of the properties of the living biological tissues. In order to create such high degree of realism, the Surgical Theater includes a Real Image Generator add-on (RIG): a visual system where patient-specific images of the surgical site, together with surrounding tissues, is realistically presented and can be manipulated in this all-purpose manner, as described below.

First, the image is segmented into "digital meshes" and/or "volumetric models" that are processed through a visual rendering engine;

Next, digital meshes and/or volumetric models are further transformed by the addition of various tissue-specific attributes such as light reflection, texture, shine, and so on to create realistic visual rendition of the surgical site; and Finally, the enhanced image is processed for alterations (cutting, pushing, clamping and so on) that will be applied by the surgeon during simulation.

The Realism Image Generator (RIG) is created by adding layers of texture, color, shine, and so on to the 3D CT/MRI imagery. This add-on presents the surgeon with an organ image that he is familiar with, and observes during the open/classic surgery. For example, the Realism Image Generator creates an image of a brain tumor that realistically represents how the brain tumor looks like in open/classic surgery—including the tumor's textures, color, and shinnies as it appears to the surgeon eyes during a real surgery.

The RIG is the visual rendering engine in the Surgical Theater that is capable of converting 3D MRI and CT patient-specific images into computerized segmented modules representing anatomical structures and features, e.g. blood vessels, brain specific tissues, neural tissues, a tumor and its encasement, etc. Secondly, the computerized segmented modules, i.e. "digital tissue mesh" are prepared for manipulation such as cutting, pushing and abrasion by the digital "surgical tools". The changes due to the "digital tissue" manipulation behave according to the tissue's physical and mechanical properties. The RIG contains a comprehensive database and repository of specific tissue attributes such as color, texture, light, brightness and so on. The repository of such attributes part of the visual engine (RIG) and facilitates developing other surgical strategies (aneurysm repair, brain shunts and so on).

RIG Design Characteristics in the Example Embodiment

The design of Surgical Theater is partly based on Flight Simulation architecture competencies such as Distributed Interactive Simulation (ST-DIS). This architecture enables pioneer and exclusive abilities to deliver a premier fidelity of the simulated scene, an essential requirement for creating immersive scenarios that are important for the rehearsal of open/classic surgeries where the surgeons interact with the organ by direct human sense. The design of the Surgical Theater facilitates a unique and exclusive ability for premier fidelity, fine cues, and computing capabilities while handling terabytes of information under hard "real-time" constraints and maintaining real-time performance (less than 100 to 150 millisecond latency), the core capability of the Flight Simulation technology. One of the features of the Distributed Interactive Simulation (ST-DIS) network and simulation architecture is that there need be no central server or processor; each simulation node (such as the RIG) maintains its own copy of the common virtual environment e.g., vessels, tissues and other models that are held and maintained at each of the simulation nodes; each such model is handled as a separate "Entity". The ST-DIS architecture allows the extended flexibility in the modularity of the development of each one of the system nodes with straightforward integration with the other system nodes through the ST-DIS network. The ST-DIS related modularity allows the development of the subsystems (nodes) separately from the other subsystems as far as a unified ST-DIS network protocol is maintained throughout all the subsystem requirements.

The following is an initial list of the RIG system characteristics:

Characteristics A—the features that RIG supports within the ST-DIS network include the "Entity State", "Environment, Cut and Shift", "Autonomy of Simulation Nodes", "Transmission of 'Surface Truth' Information", and "Transmission of State Change Information Only" categories discussed above.

"Dead-Reckoning Mechanisms" is the mechanism of determining new states based on previous ones, i.e. by extrapolation—only when the entity's (i.e. Vessel, Tissue or Tumor) true data differs enough from the extrapolated data (by a predetermined threshold) the new state is issued and distributed to the peripheral simulation nodes.

Characteristics B—The common Package Data Unit (PDU) that the RIG supports in the ST-DIS network include that listed in Table 1 above.

Characteristics C—Additional PDUs that the RIG supports when working in the ST-DIS network include are of the types listed in Table 2, above.

The Rig Architecture Block Diagram:

As outlined, the visual rendering engine restructures the 3D MRI/CT patient-specific images and creates computerized segmented visual models that represent realistic anatomical structures and features of the particular organ.

Characteristics D—The RIG includes the following features:

1. Shadow and Shadowing—shadow of an entity (i.e. Vessel, Tissue, Tumor and surgery tools) is determined by the material and peripheral orientation of the light source, light characteristics (wavelength, magnitude, and so on), and shadowing of a specific entity on another entity.
2. Texture and Coloring—Impart appearance and desirable surface characteristics; smoothness, roughness, color, surface quality, and texture of an entity (e.g., Vessel, Tissue, or Tumor).
3. Brightness—The coordinate in the color model that determines the total amount of light in the color. The brightness of an entity will be determined by the light orientation and characteristics, the entity material and current state as well by the shadowing condition.
4. Materials' Characteristics—material appearance, features, and function that are contributed by the entity's material characteristics and that are inclinational on the entity appearances, for example, light reflection of a metal surgery tool.
5. Dynamic Surface—Adaptive of all of the above features with coloration of interaction with other entities and correlation with the simulation phases', state and dynamic progress, i.e., changing tissue texture when it is being pressed creating "bloody" tissue appearance.
6. Additional requirements—engineering specifications that include parameters for real-time performances such as frame rate, latency, communication rate, as well as visual specifications such as resolution, field of view, and interfaces to graphic accelerator and to the projection system.

Figure 5:
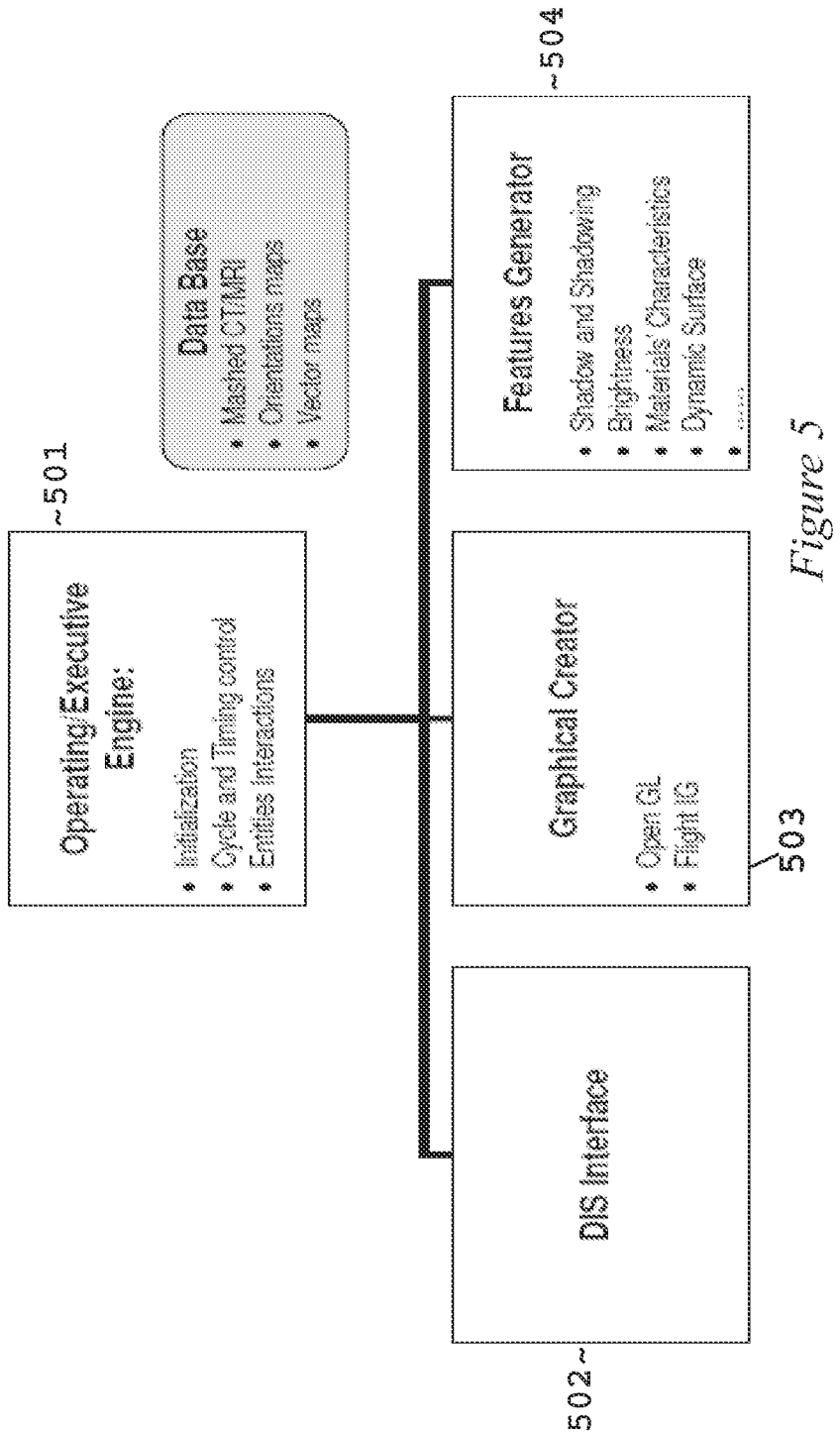
FIG. 5 provides an example high-level Realistic Image Generator (RIG) platform.

FIG. 5 shows a RIG Architecture Block Diagram. Data Base box—collection of the mesh modules based on the patient-specific CT/MRI, 3D and segmented images, pre-processing of the images, smoothing, masking, scaling. Graphic Creator box—Interface to the graphics card. ST-DIS Interface box—Interface to the ST-DIS network.

The RIG within the Surgical Theater System Block Diagram (FIG. 5):

FIG. 5 shows a hierarchy diagram of the visual systems. The system includes an executive program that runs and manages all the system components and updates the statutes of the sub components according to the surgeon/operator and the status of all the sub components as they are read through the DIS network (502). The Operating/Executive Engine (501) is responsible for the initialization of all the software and hardware components in a way that all the system's components are working with the same data bases (for example, the set of tolls that the surgeon choose). When the scenario starts, the Operating/Executive Engine (502) performs the cycle and timing control and perform the task of managing each component to complete its calculation cycle within the time frame that it is planned on in a way that all the system's sub components receive the information from the other sub components on a timely manner allowing the overall system to complete the simulation cycle in a given time frame. For example, when an action is taken by the surgeon and transmitted by the DIS network (502), the Feature Generator (504) reads the relevant part of this action/consequence of this action as calculated by the mechanical properties algorithm, the Graphic Creator (503) change the image according to this action (for example, move a vessels that was pushed by the surgeon), then calculates the changes that need to be applied on the image as a result of this change, for example, creating a shadow resulted by the change of the vessel location and orientation. This cycle is executed rapidly and continuously managed by the Operating/Executive Engine (501) in a cyclic manner in a way that each cycle is completed within a frame time of milliseconds allowing the surgeon/operator to receive real time and realistic cues.

The system process starts with standard DICOM format patient-specific images processed through a series of Reconstruction & Segmentation conversion algorithms that creates a database of Entities which the system's components can access. One of those system components is the RIG which acquires the Entities and converts them into realistic visual models with features that deliver fine cues such as shadowing, texture, material properties that assigned to the visual image models. The result is a realistic and fully immersed 3D visual environment. Additionally, the RIG is capable of processing large volumes of visual database models under hard real-time constraints while maintaining the image quality and realism. Therefore, the performances of delivering the visual fine cues are stable, steady and robust during the entire RIG envelope of operation. The additional system's components shown in FIG. 5 add and integrate features of the specific human tissues and structures with the models based on physical and mechanical properties. Once this patient-based model is set in motion in the virtual world a set of virtual surgical tools are introduced allowing the surgeon to manipulate (push, cut and etc) those models similar to a real tissue manipulation which surgeon performs during real surgery providing an intuitive experience for the user.

"Materials' Characteristics" of the Features Generator 504 shown in FIG. 5, is the application of physics-based mathematical models of the tissues that are used to produce high-fidelity simulation of physical events, such as tissue cutting and shifting. "Dynamic Surface" refers to the ability of simulation events and Entities to alter the surface database in ways that are of importance to the simulation. "Dead-Reckoning Mechanisms" is the mechanism of determining new states based on previous ones, i.e. by extrapolation—only when the entity's (i.e. Vessel, Tissue or Tumor) true data differs enough from the extrapolated data (by a predetermined threshold) the new state is issued and distributed to the peripheral simulation nodes.

Architecture and Workflow of Surgery Rehearsal Platform (SRP)

Glossary of Terms and General Description

The DICOM to "The Model" process is an offline process that reads in the DICOM data files, and converts the 2D set of images to a 3D volumetric model with attributes, that is both presentable (using the IG) and manipulateable (using the UIIE). The ST DICOM Volume Viewer is the application used for this process. Along the process pipeline the data undergoes an image enhancement stage utilizing mathematical algorithms to increase resolution and reduce noise without affecting the ability to distinguish between different tissue types. After the image enhancement stage comes the Volume of Interest (VOI) definition stage. Using the 3 panel view window in this ST DICOM Volume Viewer, the surgeon marks and defines the volume of interest around the area that needs his medical attention. (Aneurism, tumor, etc'). The next stage in this pipeline is tissue segmentation. In this stage the system uses initial tissue type intensity ranges, and the surgeon tweaks them using the Top view segmentation window of the ST DICOM Volume Viewer. The end result of the process is a Volume of Interest (VOI) that good resolution and image quality and is tissue segmented. The output of this process is a data structure that is saved to a repository (per patient) and can be retrieved from disk into the real time simulation system.

The Surgical Theater simulator is based on the cycle of simulation. A volumetric model from the previous item is fed into the simulation. The cycle is composed of (1) High fidelity & realistic visual representation of the model to the surgeon using the IG, (2) Allowing the surgeon to interact and apply actions to the model using the SUI, (3) translating those interactions to a set of mathematical values that can be applied to the model using the UIIE, and (4) changing the model itself according to those actions and other relevant inputs (such as patient heart beat etc') by running the real time tissue deformation model—RTTDE. This updated model is then reflected accordingly by the IG and there goes the cycle of simulation again. This cycle of simulation is run enough times per second to produce continuity and smooth, live simulation.

IG—The Image generator (IG) presents the model to the surgeon in a realistic 3D manner, using state of the art volume rendering techniques and utilizing the latest of GPU technology. The renderer applies shading and light effects to the model based the tissue characteristics of each voxel (3D pixel) in the model using a library of shaders, effects and values associated with each tissue type.

SUI—The surgeon user interface is composed of a set of modeled tools that are replicas of the tools the surgeon is using in the operation room. This gives the surgeon the immersive feeling as if he is in the "real" operating room. Those tools are connected to the simulation that samples their location and action, and passes that data to the UIIE. When the surgeon inserts a tool into the scene, it becomes part of the volumetric model, and as such it is displayed to the surgeon by the IG. The SUI also applies force feedback algorithms to present heptic feedback to the surgeon. The surgeon fingers feel the force of his actions, further increasing the realism of the simulation.

UIIE—The user interface interpreter engine translates the messages coming from the SUI to a finite set of variables that can be applied to the volumetric model. These variables include XYZ location, XYZ velocities, type of action, other parameters specific for the type of action (Such as force and so on). This set of variables is then fed as input to the RTTDE.

RTTDE—The real time tissue deformation engine is a model that "Sits" on top of the volumetric model. The RTTDE assigns each voxel of the volumetric model its mechanical property using a database of mechanical properties suitable for those kinds of tissue types. The properties are based on studies and research performed in those medical areas. Using the correct mechanical properties per each voxel, the set of action variables received from the UIIE, and by applying FEM algorithm—the RTTDE calculates the new state of the volumetric model. This calculation is done in real time under strict hard real time constraints, so the grid of voxels which is this volumetric model, changes to reflect the new state in real time. This new volumetric model is then reflected by the IG and so goes the cycle of simulation.

Asynchronisity—This change to the model can be done in an asynchronous manner in relation to the IG. The IG displays the model to the surgeon each frame. The model is asynchronously updated by the RTTDE algorithm, and the changes will be reflected in the IG presentation the frame after the change is performed.

SDIS—Proprietary SDIS protocol is derived from the DIS communication protocol used in flight simulators for many years. The "S" stands for "Surgical", meaning that the type of data that will flow on this network is surgical related. When implementing a network utilizing this protocol, each system that is connected to this network has to comply with its rules. Each node stores the current state of data/model and responds to incoming messages by evaluating the message relevancy to this node. If a node finds a message relevant, it performs internally according to the data associated with the message. If the message is irrelevant to that node it ignores that message. All messages on this network are broadcasted to all nodes. It is the responsibility of each node to know what to do with it. This approach minimizes the amount of data that transfers on the network allowing for high bandwidth with high reliability. Messages are handled by different nodes in parallel at the same time, increasing the performance of the whole system. This protocol utilizes the fact that each node stores the data locally and can dead recon data that is updated less frequently.

ST Simulation Executive—The 3D volumetric model, The RTTDE model and the UIIE are all hosted and run under the ST Simulation Executive application. This application has a built in scheduler, and is responsible to call each model in sequence and on time, while making sure the shared memory used to pass data between them is reliable and synchronized. The ST Simulation Executive allows the simulation to have states and move between the different states—OFF, INIT, RUN and FREEZE according to the user inputs. The built in scheduler calls the appropriate function in each model based on the state of the simulation.

The SRP creates realistic "life-like" full immersion experience for the neurosurgeon to plan and physically rehearse cerebral aneurysm clipping surgery by converting patient-specific DICOM data of the surgical site and surrounding tissues/structures into a dynamic and interactive 3D model. Unlike existing surgery preparation devices, the SRP can provide: (i) fine cues of look, feel and mechanical behavior of patient-specific tissues, (ii) 3D display of the patient-specific anatomy, (iii) real-time, surgery-like manipulation of 3D tissue model and, (iv) haptic feedback to the surgeon for a "full immersion" experience. Due to the complexity of organization and mechanical properties of living biological tissues, developing such a realistic "life-like" rendition will require following sub-developments (FIG. 6): (i) DICOM Image Volume Reader (602) and Viewer with built-in segmented Volume of Interest (VOI) Model Generator (611), (ii) 3D Image Generator (IG) (604), (iii) Real Time Soft Tissue Deformation Engine (RTTDE) (612), (iv) Surgical Distributed Interactive Simulation (SDIS) Network (610) (v) Simulation Executive Application (SimExec) software (601) (vi) Surgeon User Interface (SUI) (605), and (vii) User Interface Interpreter Engine (UIIE) (613) (vi) VisChasDB database for the visual such as tools library heart beat, blood flow and others (603).

The conversion of a set of 2D patient-specific DICOM data into a segmented 3D VOI Model with accurate patient-specific tissue attributes is done using DICOM Volume Viewer (611) (proprietary software developed by Surgical Theater LLC). First, patient-specific DICOM data set undergoes image enhancement stage using mathematical algorithms adapted for a 3D dataset (603). This enhancement stage will increase image smoothness and reduce image noise without affecting the ability to distinguish between different tissue types.

Figure 8:
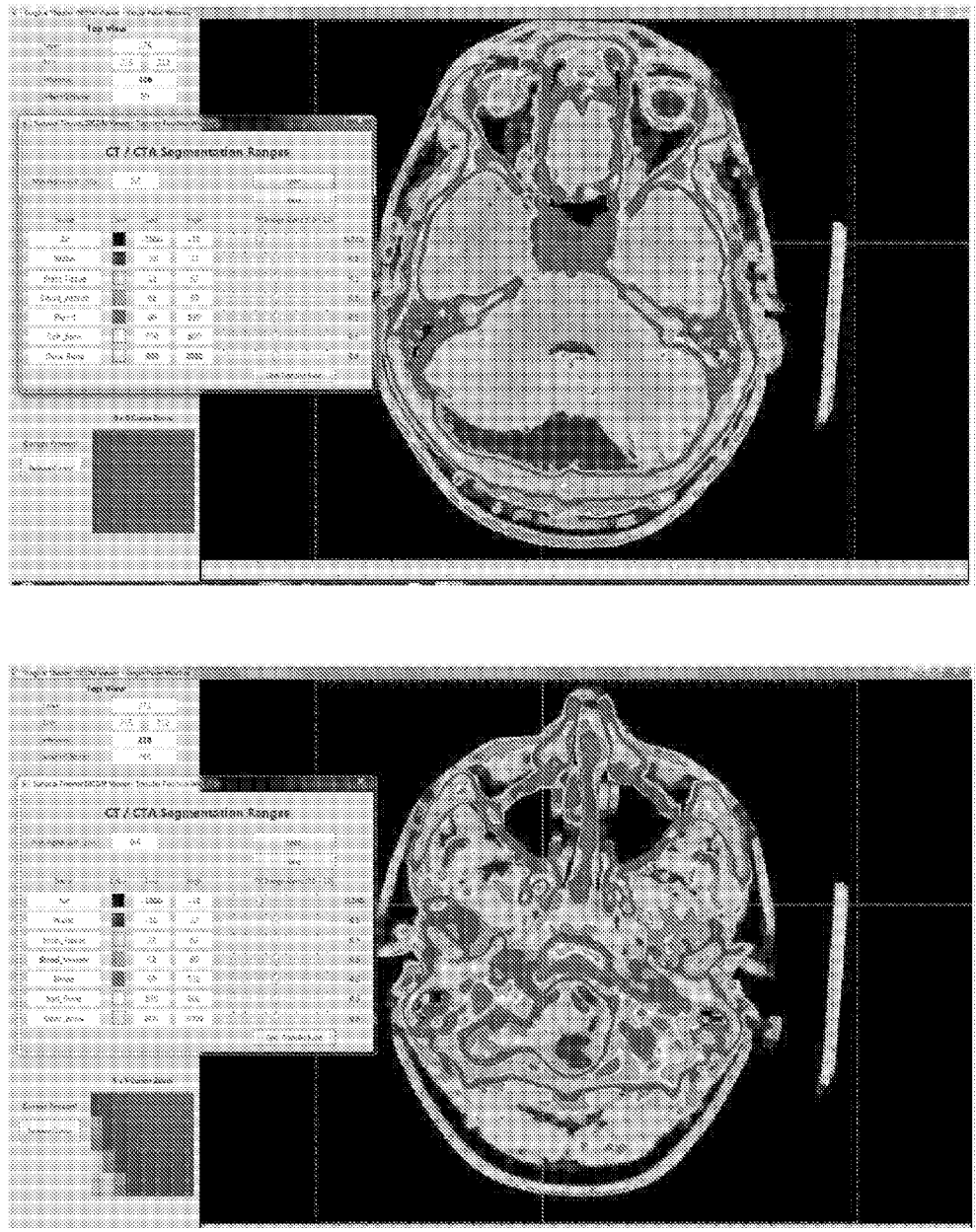

Next, using a multi-panel view window within the DICOM Volume Viewer (602), the surgeon defines VOI, i.e. surgical site containing aneurysm and surrounding vessels and structures. The next step is tissue segmentation, i.e. initial tissue-specific intensity ranges are assigned to tissues using Top View window of DICOM Volume Viewer (FIG. 8, Top) to yield 3D VOI Model (FIG. 9,) with high-resolution, quality, customizable data structure, and tissue-specific segmentation. The 3D VOI model is stored in a patient-specific repository and accessed during the cycle of operation as follows: (I) 3D Image Generator (IG) (604) presents the surgeon with high-fidelity visual representation of the model via graphical interface; (II) the surgeon manipulates the model using realistic surgical tools inside the Surgical User Interface (SUI) (605); (III) User Interface Interpreter Engine (UIIE) (613) translates surgeon's manipulations into a set of mathematical values that together with other patient-specific inputs (e.g. heart beat, blood flow and others) are applied to the model by the Real Time Tissue Deformation Engine (RTTDE) (612).

As the model changes, the IG (604) reflects those changes to the surgeon in real-time, thus completing one simulation cycle. Smooth, continuous, "life like" SRP flow is achieved by repeating cycle 60 times per second by the IG and 20 times per second by the RTTDE (612).

Preliminary Results.

Figure 6:
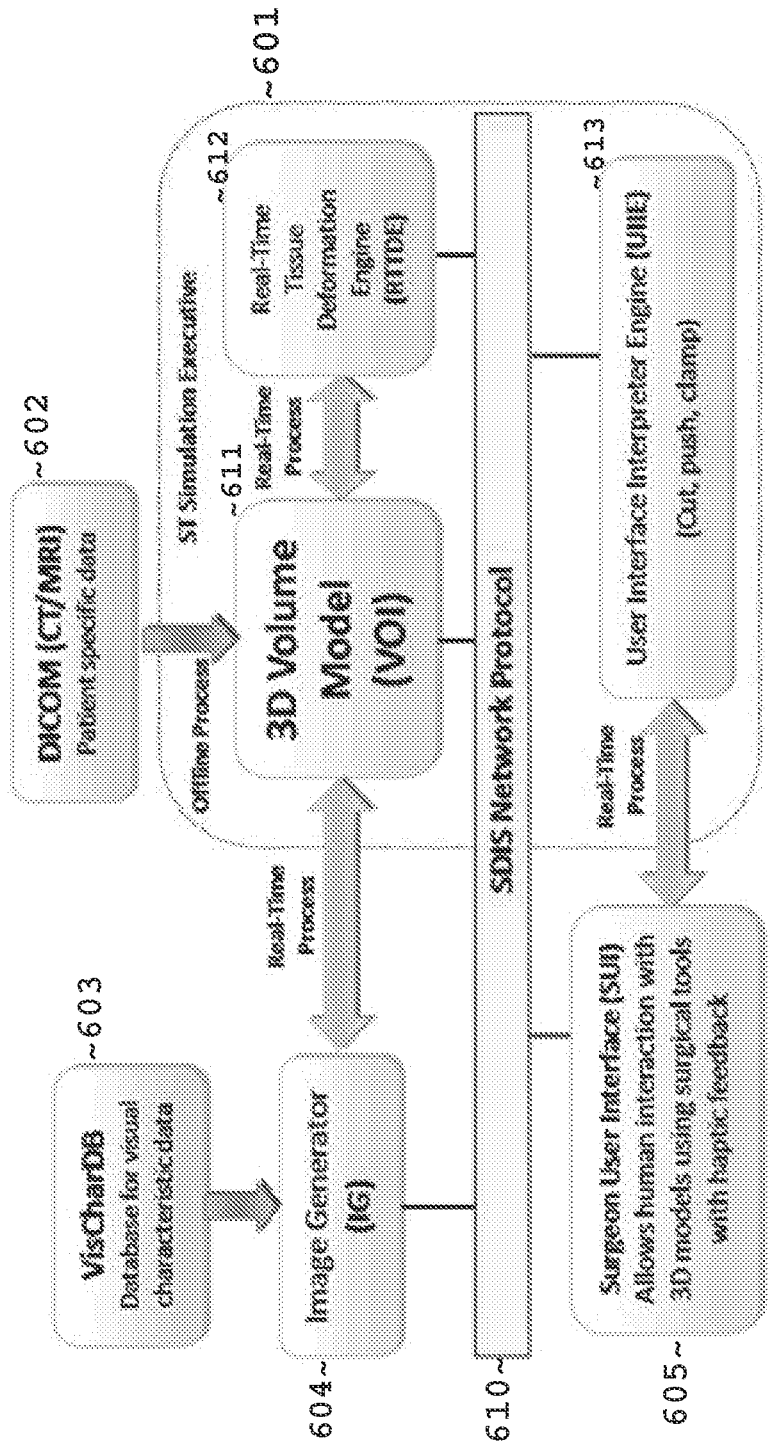
FIG. 6 provides an example high-level architecture and workflow of a Surgery Rehearsal Platform (SRP)
Figure 7:
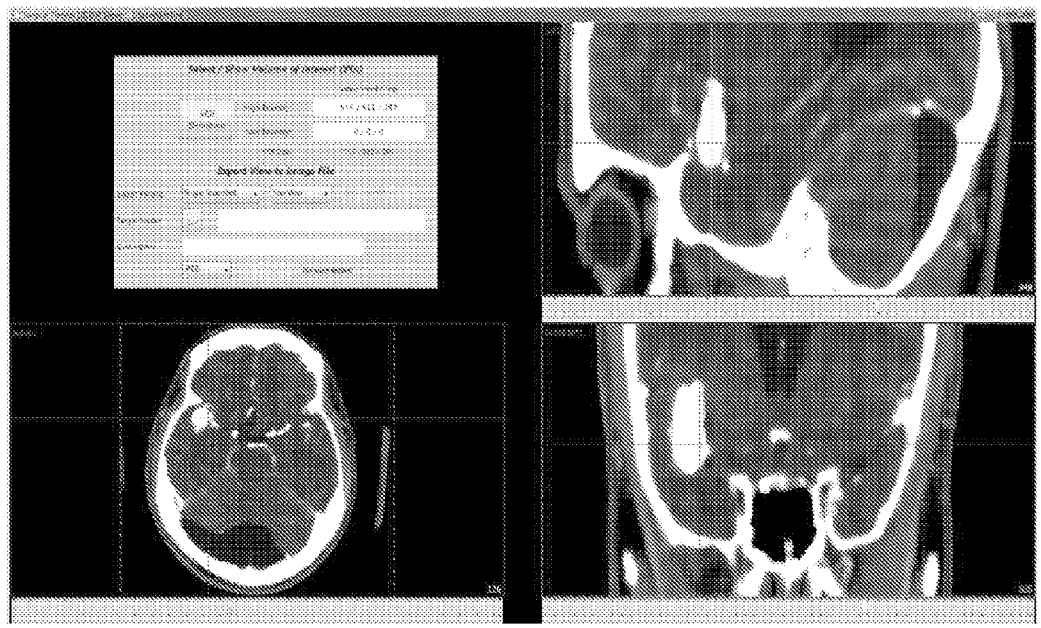
FIGS. 7-8 are example screen shots of windows in a DICOM Volume Viewer example.
Figure 9:
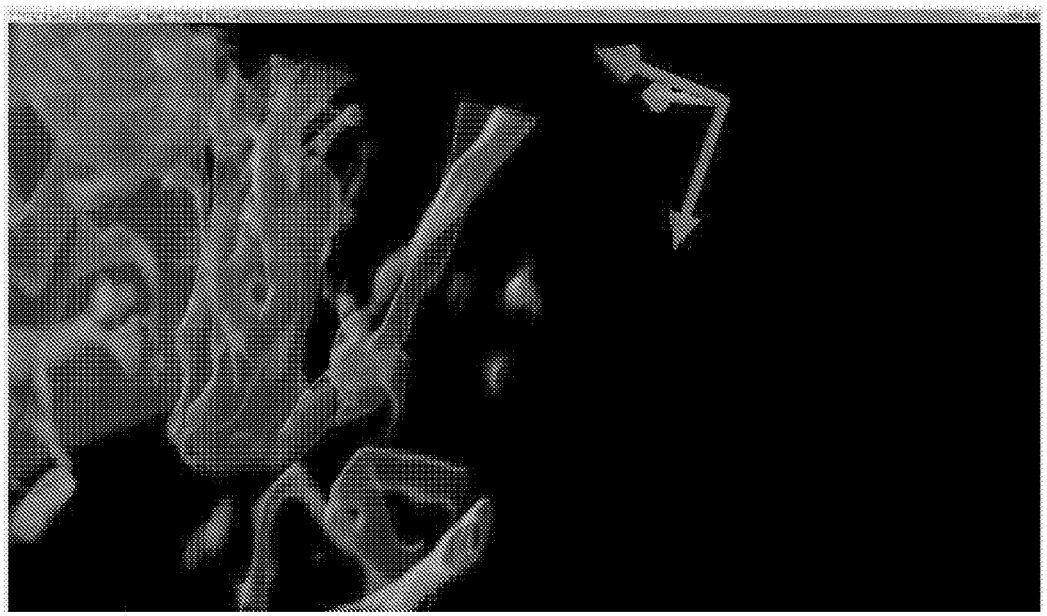
FIG. 9 shows an example screen shot of an example 3D VOI Model

At present, a working prototype of the SRP includes the following components of FIG. 6: (i) ST DICOM Volume Viewer with built-in segmented VOI Model generator (611); (ii) 3D Image Generator (IG), capable of loading and displaying the VOI to the surgeon in realistic way (604); (iii) RTTDE capable of realistically deforming tissue according to the tissue type and a set of basic of operations applied to the VOI model (cutting, retracting, dissecting, clipping, clamping) (612), and (iv) Simulation Executive software (SimExec) (601) to connect and real-time cycle the model components (i.e. SUI, UIIE, RTTDE, etc.). The IG (604) presents the model to the surgeon in a realistic 3D manner, using state-of-the-art volume rendering techniques and utilizing the latest GPU technology. The IG implements a rendering engine designed to apply fine cues such as shadowing, texture, transparency, material properties, and light effects from a library of shaders, effects, and values associated with each tissue type to the VOI model based on the tissue characteristics of each voxel (3D pixel) in the model (FIG. 9). The result will be a realistic and fully immersed 3D visual environment.

The realistic and accurate mechanical behavior of the 3D VOI model will be achieved by using Finite Element Methods (FEM) (13; 16; 17). FEM employs mass lumping to produce a diagonal mass matrix allowing real-time computation of the model's new state in space. The RTTDE (612) assigns each voxel of the VOI Model its mechanical property using a database containing tissue-specific mechanical properties that are based on medical research studies (18; 19). The change to the model can be done in an asynchronous manner in relation to the IG (604). The IG displays the model to the surgeon each frame. Then the VOI model is asynchronously updated by the RTTDE algorithm, and the changes reflected in the IG presentation. Using mechanical properties of each voxel, the set of action variables received from the UIIE and by applying FEM algorithm—the RTTDE (612) calculates the new state of the volumetric model. This real-time calculation is done under strict time constraints, so that the voxel grid representing the VOI model changes to reflect the new state in real-time. This VOI model is then reflected by the IG and so goes the cycle of simulation. The VOI model, RTTDE (612) and the UIIE are all hosted and run under the SimExec (601), which has a built-in scheduler for "calling" each model in-sequence and on-time, while ensuring that shared memory used to pass data between the running models, is reliably updated and synchronized. The SimExec allows the simulation to have "simulation states" and move between different states (OFF, INIT, RUN and FREEZE) according to user inputs.

Example Products

Product 1—Brain Surgery Theater; hardware and software package to prepare for brain surgery with proprietary libraries of tools and implant such as aneurysm clips;
Product 2—Heart Surgery Theater; hardware and software package to prepare for heart surgeries with proprietary libraries of artificial valve and tools;
Product 3—Implementing the Surgical Theater on robotic platforms;

Product 4—Implementing the Surgical Theater for additional surgeries such as bypass, orthopedic surgeries (knees, hips and so on);

Collaborative;

Implementing the Surgical Theater on Image Guided and Robot Assisted Surgery systems; and New Product Lines; Craniofacial/Plastics, ENT, Pediatric.

Example Benefits

Reduced surgical adverse events by rehearsing on patient specific with realistic immersive system; and Increasing operational efficiency by reducing surgical duration.

Wide-Ranging Benefits:

Success of a surgery highly depends, to a large extent, on the patient-specific level of preparedness of the surgeon beforehand. This is especially relevant in high-risk surgeries such as tumor removal surgery or cerebral aneurysm repair where crucial decisions are made under severe time constraints with extreme consequences. Despite long surgical residency training, the complexity and anatomical variability of the human body make high-risk surgeries such as neurosurgery one of the most challenging surgical fields. Thus, if neurosurgeons or other surgeons which perform high-risk, open/classic surgeries had an opportunity to rehearse the course of a particular patient-specific surgery, the likelihood of a successful outcome would be dramatically increased. Every year, many Americans die from medical errors and surgical errors. The ultimate goal of the surgical community is to lessen the likelihood of those errors, especially in high-risk surgeries. During recent years, the capabilities of utilizing CT and MRI images for pre-surgery preparation have evolved dramatically. Completed and high-risk surgeries, such as Neurosurgery, have also evolved into sub-specialized fields such that most brain tumors, as an example, are operated on by a small number of specialists who perform hundreds of cases per year rather than many who perform only 2-3 operations per year. However, currently, surgeons who perform high-risk open/classic surgeries use only small number of the 3D CT and MRI computerized imaging capabilities to prepare for surgeries, as those imaging technologies offer minor benefits standing alone. The Surgical Theater study concluded and recognized that the surgeons are lacking a rehearsal and preparation tool that would provide them with a realistic visual and manipulatable model with physical properties all integrated into a full immersion tool of the surgery, patient specific, rehearsal and encompassed with a preliminary realistic visual rendering engine capable of: (i) reformation and segmentation of original patient-specific 3D MRI and CT imagery into 3D meshes and/or volumetric models of components (vessels, tissues, etc.) and realistic "life-like" 3D display of the patient-specific surgical area (encompassing features such as shadow and shadowing, texture, and other features as further detailed later in this document), (ii) surgical tools for performing virtual surgery, "surgery-like" manipulation of the 3D meshes and/or volumetric models (cutting, pushing etc) based on tissue specific physical and mechanical properties using simulated surgical instruments, and (iii) feedback information to the surgeon. Therefore, the Surgical Theater is a patient-specific, high fidelity computerized simulation system that allows surgeons who perform high-risk surgeries to develop tailored strategies toward a specific surgery.

The Surgical Theater is capable of maintaining high fidelity real-time visualizations and physical modeling of large volume information traffic that is critical for the desired immersion. The Surgical Theater utilizes premier modeling fidelity technology, useful for modeling high-risk/high-workload scenarios common to both flight and the high-risk surgeries. The Surgical Theater creates fully immersive environments that comparable to Flight Simulation, where the pilots are made to feel as if they were flying a real airplane during a real mission.

Surgical Theater WPF DICOM Volume Reader Architecture and Processing Pipeline

Image Loading Pipeline:

The WPF DICOM Volume Reader (WDVR) is a WPF.NET application.

The application loads the DICOM data set (Usually a folder with many *.DCM files) into a 5 stage pipeline:

Analyze Files into List<ST_FileInfo> fileslist.

Read all the *.DC M files in the selected folder. Collect all the tags for each file. Note that the files in the folder are not always sorted. In the file metadata, one of the tags indicates the layer number for that file. In the next stage we will sort the layers. This stage also validates the files data to be valid DICOM files.

Load Files into ST_LayerData[ ] LayersVolumeOriginal.

Using the names in List<ST_FileInfo> fileslist, Read the pixel data from the *.DC M files in the selected folder. Since we now know the Layer number for each file, and the maxLayerNumber, we can allocate ST_LayerData[ ] LayersVolumeOriginal and put each files metadata and pixel data in the proper layer index.

Apply Pixel Intensity Filter into ST_LayerData[ ]LayersVolumeWorking_1.

Using the filter settings in the combo boxes, apply the intensity filter on ST_LayerData[ ] LayersVolumeOriginal. The result goes into ST_LayerData[0]LayersVolumeWorking_1, to maintain an unchanged original copy, in case we would like to apply a different filter settings later.

Apply Hounsfield Scale adjustment into ST_LayerData[ ]LayersVolumeWorking_2.

Using the Hounsfield Scale setting in the combo box, apply the Hounsfield Scale adjustment on ST_LayerData[ ]LayersVolumeWorking_1. The result goes into ST_LayerData[ ]LayersVolumeWorking_2, to maintain an unchanged Working_1 copy, in case we would like to apply a different Hounsfield Scale setting later.

Create Bitmap Sources for 3 view panels

Using ST_LayerData[ ]LayersVolumeWorking_2 create the bitmap sources and display the 3 view images. Use the sliders in the Display Window to determine the image index displayed per each panel.

Exit points from the pipeline

Although the WPF DICOM Volume Reader (WDVR) is used to display the DICOM data as a set of images, the main purpose of the application is to create the basic datasets for further processing on the Surgical Theater product.

"Cerebral Aneurysm Repair Surgeries" Case Study

During the course of cerebral aneurysm repair surgeries, the absolute orientation of the brain tissues is significantly altered as the surgeons are pushing and cutting tissues to approach the aneurysm area. Therefore, the current utilization of the advanced surgery aiding systems such as Image Guided and Navigation Systems which are based on pre-registered 3D images are limited in assisting the surgeons. Also, as surgeries, such as, for example, aneurysm repair, can be extremely time-sensitive, i.e. due to various procedures such as temporary vessel clamping to the aneurysm area, the efficiency of the procedure is highly critical and detailed planning based on the local geometry and physical properties of the aneurysm is fundamental.

To achieve a new level of pre-surgery preparation, 3D, CT, and MRI images are being increasingly utilized. However, those capabilities offer minor benefits standalone for surgery rehearsal. We recognized that the surgeons lacked a "full immersion" surgical rehearsal tool that encompasses a realistic visual model with physical tissue properties: (i) realistic "life-like" 3D display of the patient-specific aneurysm (ii) modeling of the local aneurysm geometry and physical properties (iii) interface to modeled surgery tools and clips and an ability to manipulate the aneurysm model and virtually perform surgical actions such as cutting, shifting and clamping, and (iv) interface to provide feedback information to the surgeon. Therefore, the Surgical Theater provides a patient-specific computerized modeling simulation system that allows neurosurgeons to develop tailored strategies in cerebral aneurysm repair surgery and to plan and rehearse toward the surgery with dynamic tissue and vessels modeling.

The Aneurysm Surgical Theater modeling is integrated in a fully immersive surgical rehearsal environment—the Surgical Theater system with graphical and emulation packages. The Surgical Theater (ST) utilizes premier modeling fidelity technology for high-risk/high-workload scenarios common to both flight and the high-risk surgeries.

"Brain Tumor Removal Surgeries" Case Study

According to the National Cancer Institute, in the United States, there are over 20,000 estimated new brain tumor cases found yearly, ultimately responsible for over 13,000 deaths per year. Brain tumors are the leading cause of death in children under 20 years old and second leading cause of death among males 20-29 years old. There are over 100 different types of brain tumors making effective treatment challenging. Current treatments include radiation therapy, chemotherapy and surgery. The overall cure rate for brain tumors is significantly lower than for any other types of cancer due to rapid tumor growth, difficulty of early diagnosis, and treatment ineffectiveness. However, surgery remains the most common choice for tumors that can be removed without affecting vital physiological functions. Brain tumor removal surgery is considered primary line of action because of the vast importance of the brain function, rapid tumor growth, and malignancy.

According to the Brain Tumor Foundation, annually in the United States, there are over 45,000 brain tumor removal surgeries performed. Benefits of a brain surgery include (i) removal of malignant tissue, (ii) accurate tumor diagnosis and prognosis, (iii) elimination of tumor associated symptoms (e.g. intracranial and local pressures, and (iv) time-sensitive and effective treatment of cancer to avoid death and malignancy; v) increased tolerance to adjuvant therapy.

However, perhaps more than any other sort of surgery, there are sizeable risks of performing a brain tumor removal surgery. Risks highly depend on the anatomical location of the tumor and its spread within the brain tissue. Besides common surgical risks, the main risk specific to brain tumor removal surgery is the loss of neurological tissue that controls physiological functions such as the senses, movement, coordination, memory, etc. To lessen the unnecessary risks, the neurosurgeon prepares for the surgery in a patient-specific manner, i.e., carefully studying available 3D CT and MRI images of the tumor site (as well as functional imaging with f-MRI and PET technologies). In addition, "brain-mapping" is done to identify vital regions that are adjacent to the tumor site and maybe effected by the surgery. However, currently neurosurgeons are limited to a "mind's eye view" of the three-dimensional anatomy in utilizing the 3D CT and MRI as standalone imaging technologies. We recognized that the surgeons were lacking a preparation tool that would provide full immersion into the visual and physical properties of the surgery and encompass: (i) realistic "life-like" 3D display of the patient-specific surgical area, (ii) surgical tools for performing virtual surgery, and (iii) feedback information to the surgeon.

Neurosurgeon training has been made more successful through hands-on immersive real surgical experiences that occur during residency and other training. Studying 3D patient-specific MRI and CT images does not provide "full immersion" or "realistic feedback" to the surgeon, so he/she relies heavily on the medical school and years of residency hands-on training. Thus, the need for "Patient-Specific Surgical Simulator" has become evident. Currently, there are no surgery rehearsal systems in the market that allow preparation for high-risk, classic, open surgeries on patient-specific modeling. Current simulator products utilize generic images of the brain or tools that represent 3D imagery which is lacking realistic and dynamic organism modeling and interactivity of this modeling to the procedure/actions taken by the surgeon.

The Surgical Theater creates a realistic three dimensional (3D) image with dynamic modeling of the patient's brain organisms (a "Virtual Patient"), including the tumor, brain tissue and blood vessels that will be accessed during the course of the surgery. Additionally, the Surgical Theater is able to model potential challenges that may develop during the surgery, including brain swelling, damage to blood vessels, brain tissue shifting during an operation and blocking access to the remaining parts of the tumor and others. Simulating these events in the most realistic environment possible enables the surgeon to properly prepare for such situations in the real surgery. Existing simulator products focus on "scopic" procedure simulation, used for training and education and are lacking real-time processing of a large information volume, and limited organism simulation with low fidelity. "Scopic" procedures provide no realistic visual due of their nature.

The Surgical Theater enables to build the optimal surgery plan, setting up the most efficient path to the tumor, causing the least damage to the surrounding tissues, all objected to achieve best surgery outcome with minimal risks.

1. Sample 1: Result of Patient Specific Dynamic and Interactive Image

Figure 10A:
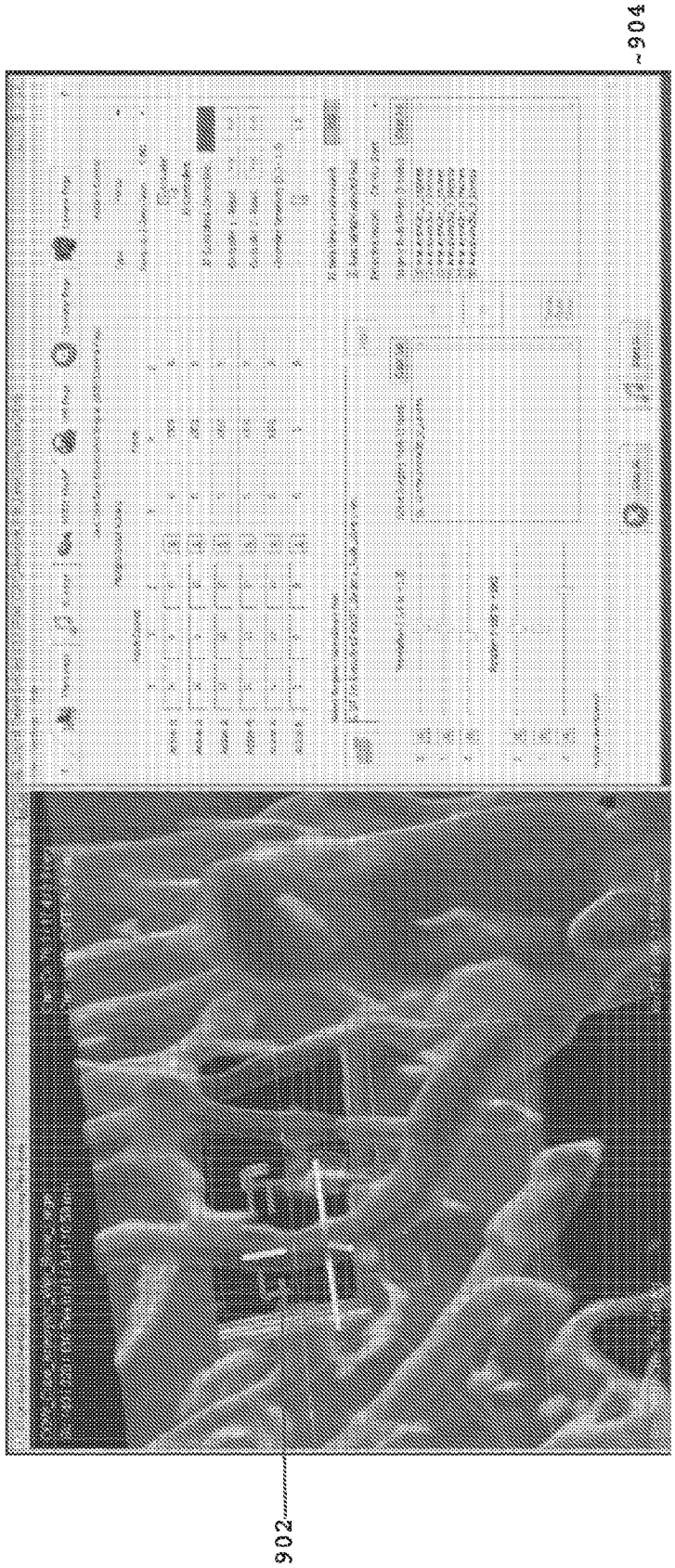
FIGS. 10A-10B are example screen-shots of an example rendered 3D tissue model.
Figure 10B:
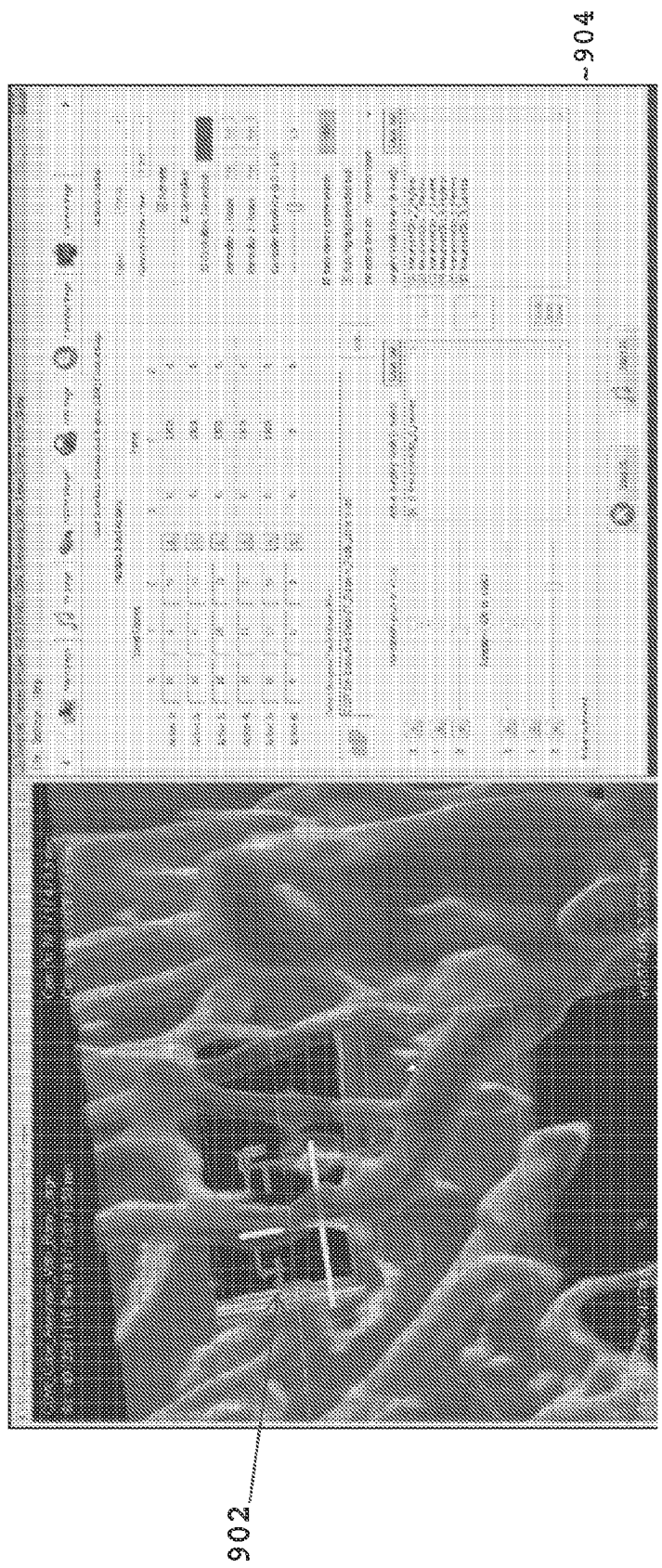
Figure 11A:
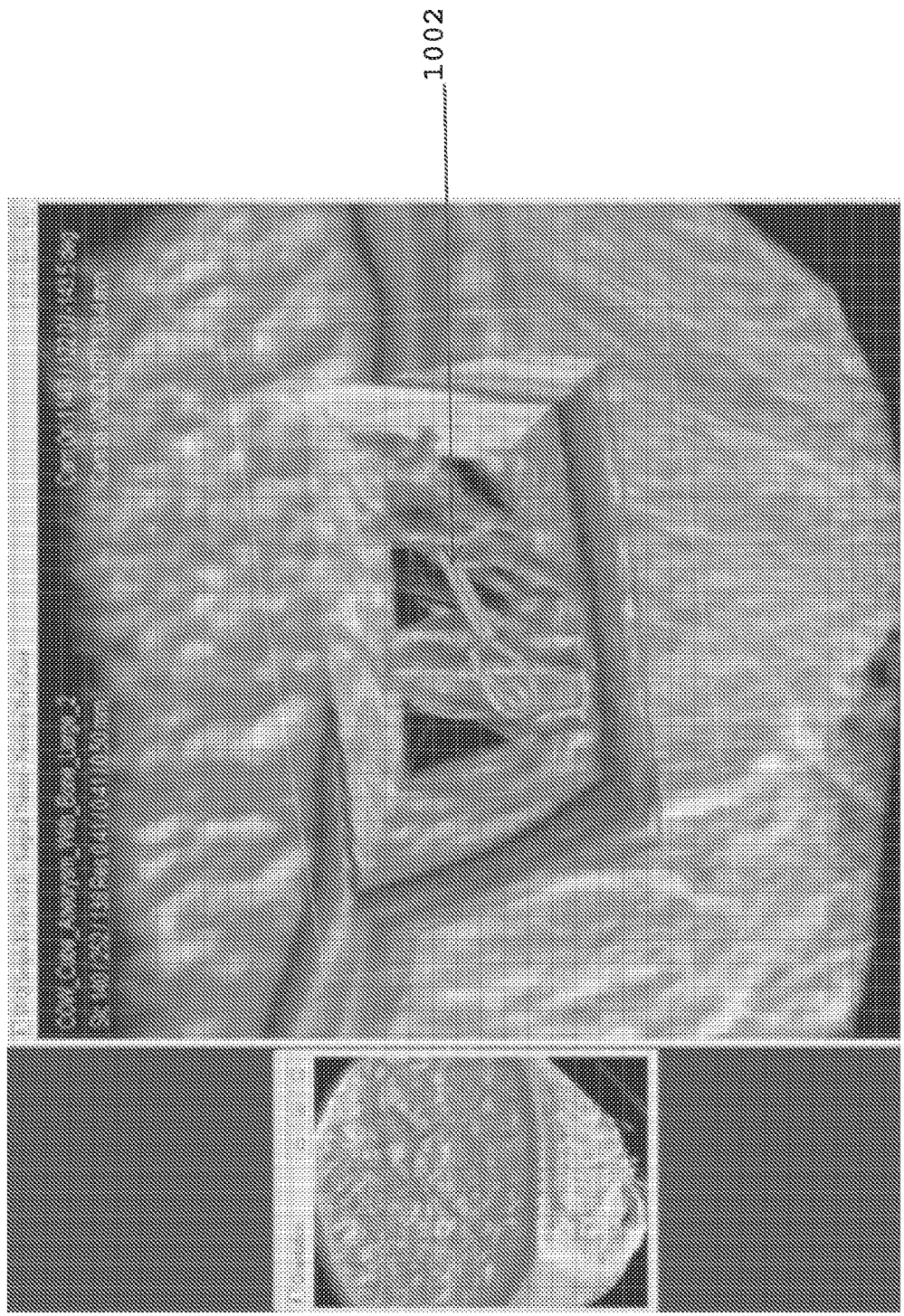
FIGS. 11A-11D are example screen shots showing an example rendered 3D tissue model with simulated tool interactions.
Figure 11B:
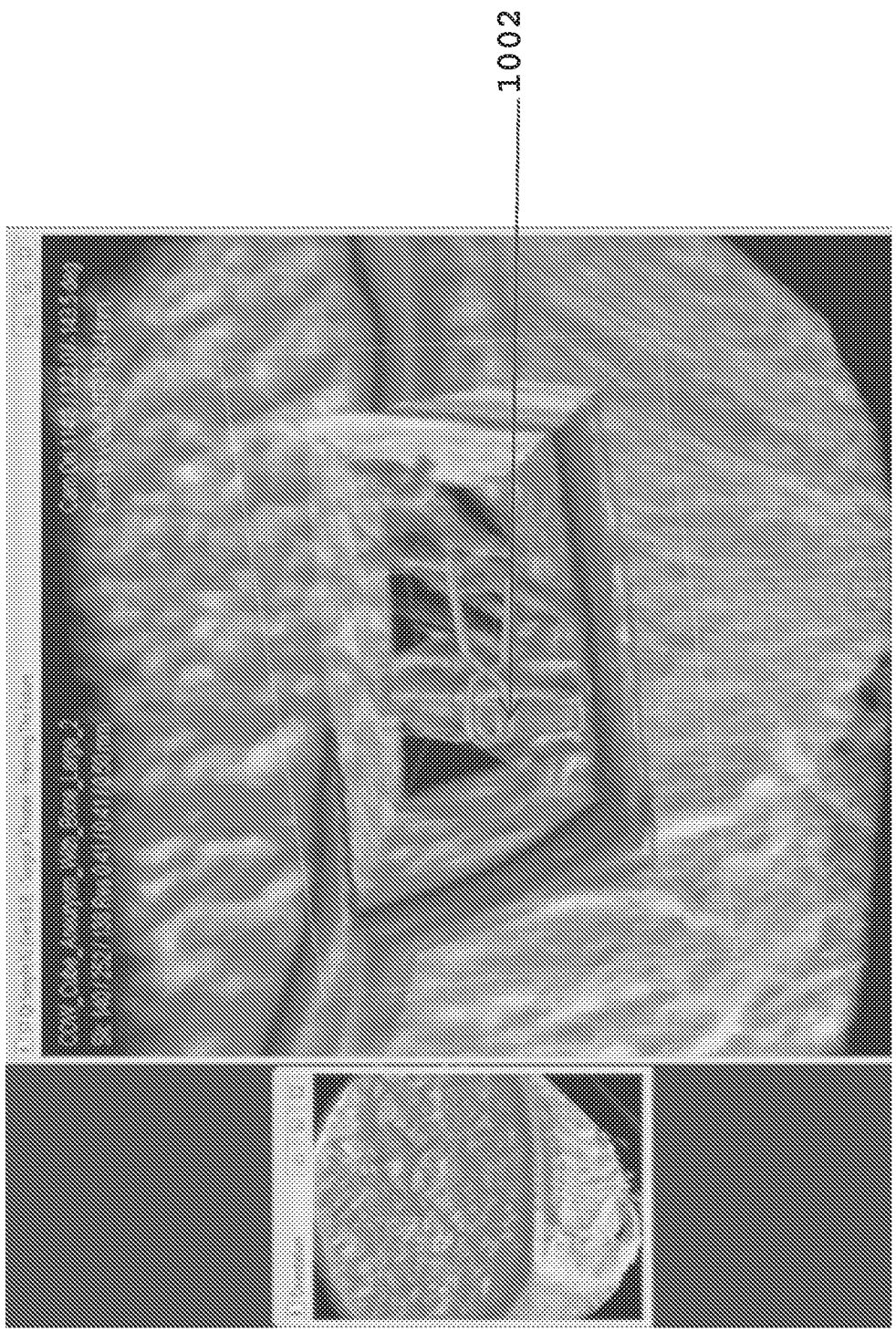
Figure 11C:
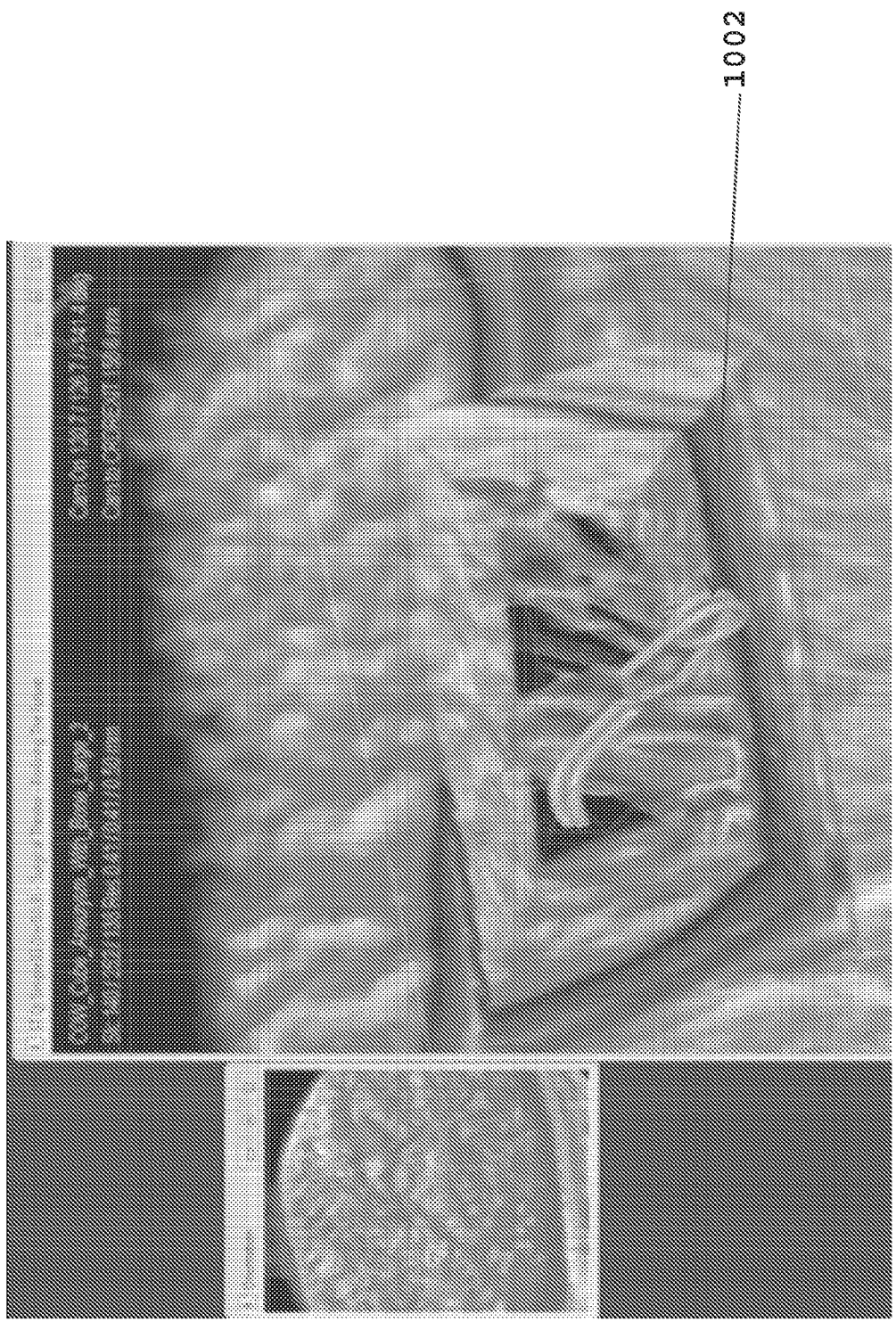
Figure 11D:
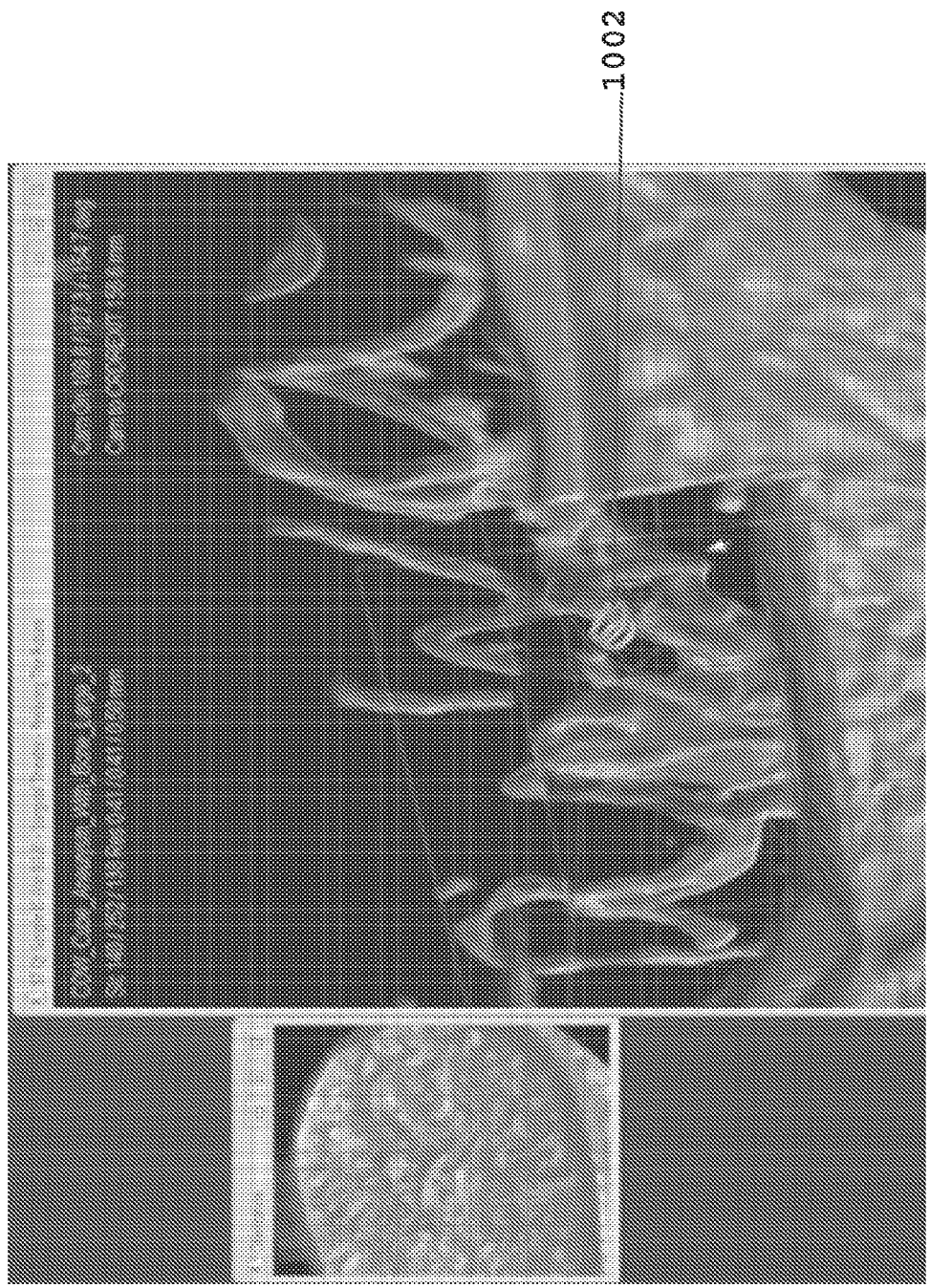

FIGS. 10A and 10B are screen shots provided by an example "Surgical Theater" system that convents static/still medical images into dynamic and interactive images/models by coupling a model of the organ (vessels, tissue, bones, fluids, etc.) dynamic to patient specific imagery. These three-dimensional images (snap shots of dynamic and interactive images) originated from a patient specific scan (in this case a CT scan). The system converted the scan into a dynamic and interactive image/model. The marked box cursor 902 (purple in the example embodiment, as shown in the priority document(s), incorporated by reference) indentifies the area of where a force is applied (by surgical tool or other means) the dynamic and interactive modeling that is based on organ, vessels, and tissues mechanical properties reactions to force when applied, resulting in dynamic movement and reshape of the organ(s) (vessels, tissue, bones, fluids, and so on) based on their actual mechanical properties model—according to the actual dynamic behavior and the mechanical properties and the dynamic behavior of actual human tissues in the specific area where the force is applied as well as mechanical properties of the surrounding organ(s) (vessels, tissue, bones, fluids, and so on).

As the examples in FIGS. 10A and 10B can demonstrate, the force that is applied causes a dynamic mechanical reaction on the vessels and tissue and the vessels are dynamically reshaped according to the corresponding vessels and tissues mechanical properties in a real patient. After the force releases, the vessels and tissues dynamically return to their original shape and location—according to the real-life dynamic behavior of corresponding vessels and tissues mechanical properties and the dynamic behavior of the mechanical properties of surrounding organ—tissues, bones, liquid and so on, and, according to any change in their surroundings. For example, if an aneurysm clip is applied on a vessel (as the a following example shows, but is true for all kind of implant and surgery tools; heart valves, grafts and so on), the force/stress that the clip makes on the vessel is reflected by the vessel's mechanical reaction to this force according to the real-life dynamic behavior of the vessels and tissue, and is thus reflected in the model and the corresponding image. Other consequences mechanical characteristics of this clip are modeled and affect the dynamic and interactive image/model, such as changes to surrounding organ that the clip may provide a force on. In FIG. 10A an aneurysm clip is shown in its "close" status, after a force was applied by the surgeon/operator, the clips reacts according to its realistic mechanical properties modeling, and, change its status to "open" as can be seen in FIG. 10B The right window provided in the screen shots are a control panel 904 of the system that allows a developer to load different patient cases and control the system's modes of operation.

Sample 1 Result of Patient Specific Dynamic and Interactive Image with Dynamics Surgery Implant (Example of Brail Aneurysm Clip)

FIGS. 11A-11D provide a serious of screen shots of the example "Surgical Theater" system that convents static/still medical images into dynamic and interactive images/models by coupling a model of the operative organ(s) (vessels, tissue, bones, liquid and so on) dynamic to patient specific imagery. The three dimensional images provided in FIGS. 11A-11D originated from a patient specific scan, and thus are adapted to the specific patient.

This set of screen shots 11A-11D demonstrates the dynamic modeling of an actual aneurysm clip; the modeled aneurysm clip 1002 shows interactive and dynamic mechanical modeling based on the actual material and physical characteristics of the clip and body tissues. The clip 1002 will react to force, when applied, to open the clip, or close it, for example, all according the realistic force that needed to perform such an action in corresponding real clips (it is applicable to heart valves, grafts and other surgery implants) allowing the surgeon a prior selection of aneurysm clips before even entering the operation room, and a prior plan of optimal approach to the feeding vessels. The example system provides realistic tactile feedback back to the surgeon to simulate the feel of an actual operation in a realistic manner.

The Surgical Theater allows the surgeon to realistically: perform "what if" scenarios; evaluate different surgery strategies; evaluate different styles or types of clips; and evaluate different approaches. The surgeon can use the system to plan and test the optimal placement and orientation of a chosen aneurysm clip to maximize the exclusion of the aneurysms from the cerebral circulation while minimizing the stress on the surrounding vessels. Similarly, the system can be used to choose the most appropriate heart valve, among the many kinds of heart valves that are available, to match with the patient own anatomy. The methodology is also applicable to grafts and other surgery implants.

The system include liberties of commercial and experimental implants (heart valves, clips, grafts and so on), allowing the surgeon to match the best applicable implant to the patient specific anatomy, and it can even allow an the implants' manufacturer/developer to improve and design a new implant.

Screen shots 11B, 11C, and 11D demonstrate a system capability to filter in/out from the visual, and from the modeling, any kind of tissue type—those snaps shots demonstrate the system capability to include or exclude (filter in/out) the soft tissue Snap Shot 10 A shows a 3 dimensional corridor crated by the system accordion to the surgeon selected location orientation and dimension of the corridor that was selected by using the system interfaces, this corridor creation is one of the steps that the surgeon performs in the simulated environment using his patient specific image/model allowing him to be ready and prepared as he will perform in the surgery, additional prior decisions that the system allow the surgeon to make is a selection of aneurysm clips to treat the aneurysm, snap shot 11A shows one clip that the surgeon choose out of many modeled clips that are available in the system's library. Snap shot 11B demonstrate the dynamic modeling of the clip and the mechanical properties that support all the clip functionality open/close status, spring load and spring force that will applied on a vessel when the clip is applied. Snap shot 11C demonstrates the availability of different kind of clips (this example shows rounded tip/end) that the surgeon can choose from. Snap shot 11D demonstrates that ability to filter in/out segment of the image, in this example, soft tissues where flittered out and only vessels are shown, this allows examination of the clip that was applied on vessel. This examination may include answering questions such as; was the whole vessels clipped as planned, where other the vessels clipped accidently and so on. This extermination is performed while viewing the interaction of the vessel and the clip without the limitation of the view that the soft tissue had on this examination and evolution.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A modeling system for enabling a user to perform a simulated medical procedure, said system comprising:
   one or more computers;
   a display for displaying images to the user;
   a database for storing physical characteristics of an organ and surrounding tissue;
   an image generator using one or more of said computers for executing software adapted for generating a dynamic realistic image of the organ and surrounding tissue for displaying on said display, wherein said realistic image is provided showing an appearance including shadowing and textures indicative of an actual organ and surrounding tissue;

a user tool library stored in said database for providing a plurality of user tool models of actual user tools used in medical procedures;

a user interface connected to one or more of said computers adapted for accepting inputs from the user for selecting one of the user tool models;

a user tool generator using one or more of said computers for executing software for generating a realistic tool image of the selected user tool model for displaying on said display; and a user interface connected to one or more of said computers adapted for accepting inputs from the user, said inputs used by said computers for dynamically manipulating said tool image for dynamically interacting with said realistic image of the organ and surrounding tissue during the simulated medical procedure for display to the user on said display in real-time, wherein the dynamic interaction between the tool image and the image of the organ and surrounding tissue is displayed on said display using images with realistic visual features exhibiting realistic mechanical interactions based on the stored physical characteristics.

2. The system of claim 1, wherein said user input interface includes a feedback mechanism for providing realistic feedback to the user, said feedback realistically representing the interactions of said tool image with said realistic dynamic images for accurately providing said simulated medical procedure.

3. The system of claim 1, further comprising a first network connected to said plurality of computers, wherein first software for executing said user tool generator, second software for executing said image generator, and third software for executing at least one of the user interface functions are each executed by one of the plurality of computers connected to said network such that at least one of said first software, said second software and said third software executes on a first one of said plurality of computers and a second one of said first software, said second software and said third software executes on a second one of said plurality of computers, wherein each one of said computers includes a sub-dataset of a database for storing a common virtual environment for increasing the efficiency of said network.

4. The system of claim 3, further comprising a host computer connected to said network, wherein, in one of said computers, a given aspect of the simulation is simulated in parallel with other aspects of the simulation that are simulated on one or more others of said computers while said network and the host computer ensure that all relevant changes in the database are shared among all of the computers, and wherein said plurality of computers are managed by the host computer for ensuring real-time or near real-time performance of said system, performed in a cyclic and rapid manner creating a continuous scenario.

5. The system of claim 4, further comprising a second network, wherein said plurality of computers and said host computer are also connected to said second network, and wherein said database is connected to said second network, such that non real-time critical network traffic is allocated to said second network and critical real-time network traffic is allocated to said first network.

6. The system of claim 4, wherein said first network is a peer-to-peer network, and wherein said plurality of computers and said host computer listen on said first network for information pertinent to their respective functionality issued by others of said computers and said host computer, and said listening computers utilize any information pertinent to their respective functionality without use of a common server.

7. The system of claim 1, wherein said image generator includes a Real Time Soft Tissue Deformation Engine (RTTDE) using finite element methods for generating said realistic dynamic images and providing said interaction that is realistically projected in the image generator and wherein said RTTDE couples mechanical properties modeling to each of a plurality of image generator image components such that the image generator updates the images according to calculations of the dynamic physical and mechanical performed and behavior of the material (for example, tissue mechanical properties or surgery tool and/or implant) by said RTTDE.

8. The system of claim 1, wherein said characteristics of said organ and surrounding tissue includes physical properties of said organ and surrounding tissue to define dynamic physical and mechanical interactions between two or more materials.

9. The system of claim 8, wherein said physical properties allow the conversion of medical images that are static into said realistic dynamic images that can interact with said tool image by coupling a model of dynamic attributes of said organ and surrounding tissue based on patient specific imagery.

10. the system of claim 1, wherein a force that is applied by the user to simulate use of the tool image in the simulation causes a dynamic mechanical reaction on blood vessels and tissues provided in said realistic dynamic images such that said blood vessels and tissues are dynamically reshaped according to mechanical properties of corresponding vessels and tissues of a real patient.

11. The system of claim 1, wherein interactions between said tool image providing a force and said realistic dynamic images of the organ and surrounding tissues are provided such that changes to surrounding organs are accurately reflected in said realistic dynamic images in a manner similar to a corresponding real surgery tool providing a similar force in an actual patient.

12. The system of claim 1, further comprising a debrief server for recording a progress of the medical procedure simulation.

13. The system of claim 12, wherein said debrief server provides an undo function to return to an earlier point in the simulation to undo recent procedures.

14. The system of claim 12, wherein said debrief server can freeze the simulation and/or change the perspective view of the simulation.

15. The system of claim 12, wherein said debrief server provides a capability to mark a point in time in said simulation for later return to that point in time to continue the simulation from the marked point in time.

16. The system of claim 12, wherein said debrief server provides a capability to replay said simulation.

17. The system of claim 1, wherein said Image generator comprises a filter for filtering out a particular type of tissue from the display of said realistic dynamic images at the request of the user.

18. The system of claim 1, wherein said Image generator includes a filter for removing a 3 dimensional corridor accordion to a desired location, orientation and dimension, of the corridor at the request of the user.

19. The system of claim 1, wherein the selected model of the surgery tool includes modeling mechanical properties of the tool that support tool open/close status, spring load, and/or spring force that will applied on a vessel in the simulation.

20. The system of claim 1, wherein said tool is an implantable medical device.

21. A platform comprising a plurality of systems of claim 1 networked together for collaboratively planning and simulating a surgery, said platform supporting users from two or more distributed sites each using at least one of said systems for supporting said surgery simulation in a coordinated manner.

22. A modeling system for enabling a user to perform a simulated medical procedure, said system comprising:
   one or more computers;
   a display for displaying images to the user;
   a database for storing physical characteristics of an organ and/or tissue;
   an image generator using one or more of said computers for executing software adapted for generating a dynamic image of the organ and/or tissue for displaying on said display;
   a user tool library stored in said database for providing a plurality of user tool models of actual user tools used in medical procedures;
   a user interface connected to one or more of said computers adapted for accepting inputs from the user for selecting one of the user tool models;
   a user tool generator using one or more of said computers for executing software for generating a tool image of the selected user tool model for displaying on said display; and
   a user interface connected to one or more of said computers adapted for accepting inputs from the user, said inputs for dynamically manipulating said tool image for dynamically interacting with said dynamic image of the organ and/or tissue during the simulated medical procedure for display to the user on said display in real-time or near real-time; and
   a debrief server for recording a progress of the simulated medical procedure for allowing the simulated procedure to return to a previous point in time for restart or replay of the simulated medical procedure.

23. A modeling system for enabling a user to perform a simulated medical procedure, said system comprising:
   a host computer;
   a first computer network;
   a plurality of simulation computers networked together via said computer network with said host computer;
   a display for displaying images to the user;
   a database for storing physical characteristics of an organ and/or tissue;
   an image generator using at least one of said computers for executing software adapted for generating a dynamic image of the organ and/or tissue for displaying on said display;
   a user tool generator using at least one of said computers for executing software adapted for generating a realistic tool image of a user tool model for displaying on said display; and
   a user interface connected to one or more of said computers adapted for accepting inputs from the user, said inputs for dynamically manipulating said tool image for dynamically interacting with said dynamic image of the organ and/or tissue during the simulated medical procedure for display to the user on said display, wherein
   one aspect of the simulated medical procedure is generated using a first subset of simulation data in one of said plurality of computers concurrent with another aspect of the simulated medical procedure being generated using a second subset of simulation data in another of said plurality of computers, and wherein
   said host computer ensures that said first subset of data is consistent with said second subset of data as the simulated medical procedure progresses, and wherein
   said host computer coordinates the plurality of computers to provide the simulated medical procedure.

24. The modeling system of claim 23, further comprising a second network, wherein said plurality of computers and said host computer are also connected to said second network, such that non real-time critical network traffic is allocated to said second network and critical real-time network traffic is allocated to said first network.

25. The modeling system of claim 22, further comprising a first network for networking said plurality of computers together, and also comprising a second network for networking said plurality of computers together, such that non real-time critical network traffic is allocated to said second network and critical real-time network traffic is allocated to said first network.

* * * * *

UNITED STATES PATENT AND TRADEMARK OFFICE
CERTIFICATE OF CORRECTION

PATENT NO. : 8,831,924 B2
APPLICATION NO. : 13/651549
DATED : September 9, 2014
INVENTOR(S) : Mordechai Avisar It is certified that error appears in the above-identified patent and that said Letters Patent is hereby corrected as shown below:

In the Specification,

Column 24, Line 4, "cycle 60 times" should read -- cycle $\geq$60 times --

Column 26, Line 33, "ST_LayerData[0]LayersVolumeWorking_1," should read -- ST_LayerData[]LayersVolumeWorking_1, --

Signed and Sealed this
Ninth Day of December, 2014

Michelle K. Lee
*Deputy Director of the United States Patent and Trademark Office*